United States Patent
Karp et al.

(10) Patent No.: US 11,458,153 B2
(45) Date of Patent: Oct. 4, 2022

(54) DRUG DELIVERY COMPOSITION COMPRISING A SELF-ASSEMBLED GELATOR

(71) Applicants: The Brigham and Women's Hospital, Inc., Boston, MA (US); The City University of New York, represented by The Research Foundation of the City University of New York, New York, NY (US)

(72) Inventors: Jeffrey M. Karp, Brookline, MA (US); Praveen Kumar Vemula, Cambridge, MA (US); George John, Edison, NJ (US); Greg Cruikshank, Sunnydale, NY (US)

(73) Assignees: The City University of New York, represented by The Research Foundation of the City University of New York, New York, NY (US); The Brigham and Women's Hospital Inc., Boston, MA (US)

( * ) Notice: Subject to any disclaimer, the term of this patent is extended or adjusted under 35 U.S.C. 154(b) by 0 days.

(21) Appl. No.: 15/213,055

(22) Filed: Jul. 18, 2016

(65) Prior Publication Data
US 2017/0035891 A1    Feb. 9, 2017

Related U.S. Application Data

(63) Continuation of application No. 13/119,304, filed as application No. PCT/US2009/057349 on Sep. 17, 2009, now abandoned.

(60) Provisional application No. 61/097,565, filed on Sep. 17, 2008.

(51) Int. Cl.

| | | |
|---|---|---|
| *A61K 47/48* | (2006.01) | |
| *A61K 31/7034* | (2006.01) | |
| *A61K 9/06* | (2006.01) | |
| *A61K 31/167* | (2006.01) | |
| *A61K 45/06* | (2006.01) | |
| *A61K 31/12* | (2006.01) | |
| *A61K 31/555* | (2006.01) | |
| *A61K 31/22* | (2006.01) | |
| *A61K 31/405* | (2006.01) | |
| *A61K 31/43* | (2006.01) | |
| *A61K 47/55* | (2017.01) | |
| *A61K 47/54* | (2017.01) | |

(52) U.S. Cl.
CPC ............ *A61K 31/7034* (2013.01); *A61K 9/06* (2013.01); *A61K 31/12* (2013.01); *A61K 31/167* (2013.01); *A61K 31/22* (2013.01); *A61K 31/405* (2013.01); *A61K 31/43* (2013.01); *A61K 31/555* (2013.01); *A61K 45/06* (2013.01); *A61K 47/54* (2017.08); *A61K 47/542* (2017.08); *A61K 47/55* (2017.08); *A61K 47/555* (2017.08)

(58) Field of Classification Search
CPC .... A61K 31/7034; A61K 9/06; A61K 31/167; A61K 45/06; A61K 31/12; A61K 31/555; A61K 31/22; A61K 31/405; A61K 31/43; A61K 47/55; A61K 47/542; A61K 47/555; A61K 47/54
See application file for complete search history.

(56) References Cited

U.S. PATENT DOCUMENTS

| | | | |
|---|---|---|---|
| 4,027,038 A | 5/1977 | Bernstein | |
| 5,603,959 A * | 2/1997 | Horrobin | ............... A61P 29/00 424/490 |
| 6,031,017 A | 2/2000 | Waki | |
| 6,471,970 B1 | 10/2002 | Fanara | |
| 7,749,485 B2 | 7/2010 | Tournier | |
| 9,452,178 B1 | 9/2016 | Hauser | |
| 9,962,339 B2 | 5/2018 | Karp | |
| 9,974,859 B2 | 5/2018 | Karp | |
| 10,300,023 B1 | 5/2019 | Karp | |
| 10,568,840 B2 | 2/2020 | Karp | |
| 11,020,410 B2 | 6/2021 | Karp | |
| 2005/0084470 A1 | 4/2005 | Abbas | |
| 2005/0220822 A1* | 10/2005 | Hoffman | ............. A61K 39/015 424/272.1 |
| 2005/0267036 A1 | 12/2005 | Garry | |
| 2005/0287198 A1 | 12/2005 | Murthy | |
| 2006/0276676 A1 | 12/2006 | van Bommel | |
| 2008/0004398 A1 | 1/2008 | Durrieu et al. | |
| 2008/0021068 A1 | 1/2008 | Alam | |

(Continued)

FOREIGN PATENT DOCUMENTS

| | | |
|---|---|---|
| AU | 2015200633 | 2/2015 |
| EP | 1063007 | 12/2000 |

(Continued)

OTHER PUBLICATIONS

F.J. Persico, et al, Effect of Tolmetin glycine Amide (McN-4366), a Prodrug of Tolmetin Sodium, on Adjuvant Arthritis in the Rat, 247 J Pharmacol. Exp. Thera. 889 (1988).*

(Continued)

*Primary Examiner* — Sean M Basquill
(74) *Attorney, Agent, or Firm* — Fish & Richardson P.C.

(57) ABSTRACT

This invention discloses drug-delivery compositions, methods of making prodrugs, and methods of drug delivery using a self-assembled gelator. The backbone of the gelator can contain a drug or prodrug, such as acetaminophen or salicin. Additional drugs or agents can be encapsulated in the gelator. Enzymatic or hydrolytic cleavage can be used to release the drugs.

19 Claims, 16 Drawing Sheets

(56) References Cited

U.S. PATENT DOCUMENTS

| | | |
|---|---|---|
| 2008/0038316 A1 | 2/2008 | Wong |
| 2009/0048296 A1 | 2/2009 | Campbell |
| 2009/0110735 A1 | 4/2009 | Maggio |
| 2009/0169498 A1 | 7/2009 | de Jong |
| 2009/0257968 A1 | 10/2009 | Walton |
| 2009/0263489 A1 | 10/2009 | Zanella |
| 2010/0129451 A1 | 5/2010 | John |
| 2012/0022158 A1 | 1/2012 | Niu |
| 2012/0040623 A1 | 2/2012 | Liu |
| 2012/0189588 A1 | 7/2012 | Nahas |
| 2013/0079371 A1 | 3/2013 | Sundberg |
| 2013/0273140 A1 | 10/2013 | Maggio |
| 2013/0280334 A1 | 10/2013 | Karp |
| 2013/0309286 A1 | 11/2013 | Engstad |
| 2014/0041378 A1 | 3/2014 | Craig |
| 2014/0302144 A1 | 10/2014 | Koutsopoulos |
| 2015/0125403 A1 | 5/2015 | Joerger |
| 2015/0202586 A1 | 7/2015 | Imoto |
| 2015/0297731 A1 | 10/2015 | Chiou |
| 2016/0243026 A1 | 8/2016 | Pathak |
| 2017/0000888 A1 | 1/2017 | Karp |
| 2017/0035891 A1 | 2/2017 | Karp |
| 2017/0100342 A1 | 4/2017 | Karp |
| 2017/0319500 A1 | 11/2017 | Karp |
| 2018/0050055 A1 | 2/2018 | Ahmed |

FOREIGN PATENT DOCUMENTS

| | | |
|---|---|---|
| EP | 0517211 | 9/2004 |
| EP | 2361640 | 8/2011 |
| FR | 2417494 | 9/1979 |
| WO | 9907416 | 2/1999 |
| WO | 2003006043 | 1/2003 |
| WO | 2005056039 | 6/2005 |
| WO | WO 2006/008386 | 1/2006 |
| WO | 2010033726 | 3/2010 |
| WO | 2012040623 | 3/2012 |
| WO | 2014041378 | 3/2014 |
| WO | 2014089472 | 6/2014 |
| WO | 2017193138 | 11/2017 |
| WO | 2017193139 | 11/2017 |

OTHER PUBLICATIONS

Indomethacin MSDS (Jun. 19, 2012).*
Amit S. Kalgutkar, et al., Ester and Amide derivatives of the Nonsteroidal Antiinflammatory Drug, Indomethacin, as Selective Cyclooxygenase-2 Inhibitors, 43 J Med. Chem., 2860 (2000).*
Takeru Higuchi, Pradeep Niphadkar, and Takeo Kawaguchi, Specificity of Esterases and Effect of Structure of Prodrug Esters of Acylated Acetaminophen on Hydrolytic Reactivity in Pharmacokinetics (L.Z. Benet, et al., eds.) (Year: 1984).*
Lara A. Estroff and Andrew D. Hamilton, Water Gelation by Small Organic Molecules, 104 Chem. Rev. 1201 (Year: 2004).*
Bennett et al., Next-generation hydrogel films as tissue sealants and adhesion barriers, Cardiac Surgery 18:494-499 (2003).
Bhattacharya et al., In Molecular Gels, Kluwer Academic Publishers: The Netherlands (2004).
Bhuniya et al., (S)-(+)-Ibuprofen-Based Hydrogelators: An Approach Toward Anti-Inflammatory Drug Delivery, Tetrahedron Lett. 47:7153-7156 (2006).
Bong et al., Angew. Self-Assembling Organic Nanotubes, Chem. Int. 40:988-1011 (2001).
Boutaud et al., J.A. Determinants of the Cellular Specificity of Acetaminophen as an Inhibitor of Prostaglandin H(2) Synthases, Proc. Natl. Acad. Sci. U.S.A. 99:7130-7135 (2002).
Bryers et al., Biodegradtion of Poly(anhydride-esters) into Non-Steroidal Anti-Inflammatory Drugs and Their Effect on Pseudomonas aeruginosa Biofilms In Vitro and on the Foreign-Body Response In Vivo, Biomaterials 27:5039-48 (2006).
Caran et al., Anatomy of a Gel. Amino Acid Derivatives that Rigidity Water at Submillimolar Concentrations, Am. Chem. Soc. 122: 11679-11691 (2002).
Chourasia et al., Pharmaceutical Approaches to Colon-Targeted Drug Delivery Systems, Pharm. Pharmaceut. Sci. 6:22-66 (2003).
Erdmann et al., Degradable Poly(anhydridie ester) Implants: Effects of Localized Salicylic Acid Release on Bone, Biomaterials 21:2507-2512 (2000).
Estroff et al., Effective Gelation of Water Using a Series of Bis-urea Dicarboxylic Acids, Angew. Chem. Int. Ed. 39:3447-3450 (2000).
Fischel-Ghodsian et al., Enzymatically Controlled Drug Delivery, Proc. Natl. Acad. Sci. U.S.A. 85:2403-2406 (1988).
Friggeri et al., Entrapment and release of quinoline derivatives using a hydrogel ofa low molecular weight gelator, Controlled Release 97: 241-248 (2004).
Frog et al., Hydrogels as Separation Agents. Responsive Gels. Volume Transitions II, Advances in Polymer Science, 67-79 (1993).
Gong et al., Synthesis ofhydrogels with extremely low surface friction , J. Am. Chem. Soc., 123,5582 (2001).
Gupta et al., Hydrogels.from controlled release to pH-responsive drug delivery , Drug Discovery Today, 7, 569-579 (2002).
Han, et al., Catalytic ester-amide exchange using group (iv) metal alkoxide-activator complexes , JACS, 127:10039-44 (2005).
Hans et al., Synthesis and characterization ofmPEG-PLA prodrug micelles , Biomacromolecules, 6, 2708-2717 (2005).
Harten et al., Salicylic acid-derived poly(anhydride-esters) inhibit bone resorption and formation in vivo , Biomed. Mater. Res-A 72A:354-362 (2005).
Hoare et al., Polymer, 49: 1993-2007 (2008).
Huang et al., On the importance and mechanisms of burst release in matrix-controlled drug delivery svstems , Controlled Release, 73:121-136 (2001).
International Preliminary Report on Patentability issued in PCT/US2009/057349 dated Mar. 22, 2011.
International Search Report issued in PCT/US2009/057349 dated May 6, 2010.
Jen et al., Review. Hydrogels for cell immobilization , Biotechnol. Bioeng.,50: 357-364 (1996).
John et al., Biorefinery. a design tool for molecular gelators, Langmuir. 26: 17843-51 (2010).
John et al., Lipid-based nanotubes asfunctional architectures with embedded fiuorescence and recognition capabilities , J. Am. Chem. Soc., 126, 15012-15013 (2004).
John et al., Morphological control of helical solid bilayers in high-axial-ratio nanostructures through binarv sell-assemble , Chem. Eur. J., 8:5494-5500 (2002).
John et al., Unsaturation effect on gelation behavior ofaryl glycolipids , Langmuir, 20:2060-2065 (2004).
John et al., AdV. Mater., Nanotube Formation from Renewable Resources via Coiled Nanofibers, 13, 715-718 (2001).
Jovanovic et al., How curcumin works preferentially with water soluble antioxidants , Chem. Soc., 123, 3064-3068 (2001).
Jung et al., Self-Assembly ofa Sugar-Based Gelator in Water. Its Remarkable Divers ity in Gelation Abilitv and Aggregate Structure, Lanumuir 17, 7229-7232 (2001).
Kalgutkar et al., Ester and Amide Derivatives of the Nonsteriodal Antiinflammatory Drug,Indomethacin, as selective cvclooxvgenase-2 inhibitors, J. Med. Chem.,43:2860-70 (2000).
Kamath et al., Biodegradable Hydrogels in Drug Delivery, Adv. Drug Deliv. Rev., 11:59-84 (1993).
Kim et al., In vivo evaluation of polymeric micellar paclitaxel formulation. toxicity and efficacy , Controlled Release, 72: 191-202 (2001).
Kiyonaka et al., Semi-wc/ peptide/protein array using supramolecular hydrogel , Nat. Mater., 3,58-64 (2004).
Kobayashi et al., Molecular design of super hydrogelators. understanding the gelation process of azobenzene-based sugar derivatives in water , Org. Lett. 4: 1423-1426 (2002).
Kumar et al., First snapshot ofa nonpolymeric hydrogelator interacting with its getting solvents , Chem. Common., 4059-4062 (2005).
Kumar, et al. Prodrugs as self-assembled hydrogels: a new paradigm for biomaterials , Biotech., 24:1-9 (2013.
Lee et al., Hydrogelsfor Tissue Engineering, Chem. Rev., 101: 1869-1880 (2001).

(56) References Cited

OTHER PUBLICATIONS

Li, et al., Molecular nanofibers of olsalazine form supramolecular hydrogeis for reductive release of an anti-inflammatory agent, JACS, 132:17707-9 (2010).
Loos et al., Design and Application of Self-Assembled Low Molecular Weight Hydrogels, Eur. J.of Organic Chem. 17:3615-3631 (2005).
Lu et al., Photopolymerization of multilaminated poly(HEMA) hydrogels for controlled release, Controlled Release, 57:291-300 (1999).
Luboradzki et al., An Attempt to Predict the Gelation Ability of Hydrogen-Bond-Based Gelators Utilizing a Glvcosidase Librarv, Tetrahedron 56:9595-9599 (2000).
Makarevic et al., Bis(amino acid) oxalyl amides as ambidextrous gelators of water and organicsolvents. supramolecular gels with temperature dependent assembly/dissolution equilibrium,Chem. Eur. J. 7:3328-3341 (2001).
Mazumdar et al., Preparation and evalulation ofethambutol derivatives, Indian J. Pharm. Sci., 47: 179-180 (1985).
Menger et al., Anatomy ofa Gel. Amino Acid Derivatives that Rigidity Water at Submillimolar Concentrations, J. Am. Chem. Soc. 122:11679-11691 (2000).
Miyata et al., Biomolecule-Sensitive ydrogels, Adv. Drug Deliv. Rev., 54:79-98 (2002).
Nicolaou et al., A Water-Soluble Prodrug of Taxol with Self-Assembling Properties, gew.Chem. Int. Ed., 33: 1583-1587 (1994).
Oda et al., Gemini Surfactants as New, Low Molecular Weight Gelators of Organic Solvents and Water, Angew. Chem. Int. Ed. 37, 2689-2691 (1998).
Peppas et al., Hydrogels in Biology and Medicine. From Molecular Principles to Bionanotechnologv, R. Adv. Mater., 18:1345-1360 (2006).
Peppas, et al., Hydrogels in pharmaceutical formulations, Eur. J. Pharm. Biopharm., 50:27-46 (2000).
Peppas, N., Hydrogels and Drug Delivery, Curr. Opin. Colloid Interface Sci. 2:531-537 (1997).
Persico, et al.,K Effect of tolmetin glycine amide (McN-4366) a prodrug of tolmetin sodkum on adjuvant arthritis in the rat, J Pharma Exp Therap., 247(3):889-96 (1988).
Poulsen, et al., Effect of topical vehicle composition on the in vitro release of fluocinolone acetonide and its acetate ester, J Pharma Sci., 57(6):928-33 (1968).
Qiu et al., Environment-sensitive hydrogels for drug dc/ivory, Adv. Drug Deliv. Rev., 53, 321-339 (2001).
Rattie et al., Acetaminophen Prodrugs III. Hydrolysis of Carbonate and Carboxylic Acid Esters in Aqueous Bu[[ers, J. Pharm. Sci., 59: 1738-1741 (1970).
Robinson et al., Design, synthesis, and biological evaluation ofangiogenesis inhibitors. Aromatic cnonc and dienone analogues ofcurcumin, Bioru. Med. Chem. Lett., 13:115-117 (2003).
Rooseboom et al., Enzyme-catalyzed activation ofanticancer prodrugs, Pharmacol. Rev., 56:53-102 (2004).
Sinha et al., Microbially triggered drug delivery to the colon, Eur. J. Pharm. ScL, 18:3-18 (2003).
Sreenivasachary et al., Gelation-driven component selection in the generation of constitutional dynamic hydrogels based on guanine-quartet formation, J.-M. Proc. Natl. Acad. ScL USA 102:5938-5943 (2005).
Toth and Urtis, Commonly used muscle relaxant therapies for acute low back pain: A review of carisoprodol cyclobenzaprine hydrochloride, and metaxalone, Clin Therap., 26 (9):1355-67 (2004).
Van Bommel et al., Two-stage enzyme mediated drug release from LMWG gydrogels, Org.Biomol. Chem. 3:2917-2920 (2005).
Vassilev et al., Enzymatic Synthesis of a Chiral Gelator with Remarkably Low Molecular Weight, Chem. Commun., 1865-1866 (1998).
Vemula et al., fincymc Catalysis. Tool to Make and Break Amygdalin Hydrogelators from Renewable Resources. A Delivery Model for Hydrophobic Drugs, J. Am. Chem. Soc., 128: 8932-8938 (2006).

Vemula et al., In Situ Synthesis of Gold Nanoparticles using Molecular Gels and Liquid Crystals from Vitamin-C Amphiphiles, Chem. Mater. 19, 138-140 (2007).
Vemula et al., Smart Amphiphiles. Hydro/Organogelators for In Situ Reduction of Gold, Chem.Commun., 2218-2220 (2006).
Vigroux, et al., Cyclization-activated prodrugs: N-(substituted 2-hydroxyphenyl and 2-hydroxypropyl)carbamates based on ring-opened derivatives of active benzoxazolones and oxazolidinones as mutual prodrugs of acetaminophen, J Med Chem., 38:3983-94 (1995).
Wang et al., how Molecular Weight Organogelators for Water, Chem. Commun. 310-311 (2003).
We der Linden et al., Clinic/us-scnsi/ive hydrogels and their applications in chemical (micro)analvsis, Analyst, 128:325-331 (2003).
Whitesides et al., Beyond molecules. self-assembly ofmesoscopic and macroscopic components, Proc. Natl. Acad. ScL USA 99, 4769-4774 (2002).
Xiog et al., J. Hydrophobic Interaction and Hydrogen Bonding Cooperatively Confer a Vancomycin Hydrogel. A Potential Candidatefor Biomaterials, J. Am. Chem. Soc. 124:14846-14847 (2002).
Yan et al., Enzymatic Production ofsugar Fatty Acids Esters, PhD thesis, University of Stuttgard, (2001).
Yang et al., ASimple Visual Assay Based on Small Molecule Hydrogels for Detecting Inhibitors of Prcrmcs, Chem. Commun., 2424-2425 (2004).
Yang et al., Enzymatic Formation of Supramolecular Hydrogels, Adv. Mater., 16:1440-1444 (2004).
Yang et al., Enzymatic Hydrogelation ofsmall Molecules, Ace. Chem. Res., 41:315-326 (2008).
Yang et al., Small Molecular Hydrogels Based on a Class ofAnti-Inflammatory Agents, Chem. Commun., 208-209 (2004).
Yang et al., Using a Kinase/Phosphatase Switch to Regulate a Supramolecular Hydrogel and Forming the Supramolecular Hvdrogel In Vivo, J. Am. Chem. Soc. 128:3038-3043 (2006).
Zhang et al., Hydrogels: Wet or Let Die, Nature Materials 3:7-8 (2004).
Zhang, et al., Versatile small-moleule motifs for self-assemly in water and the formation of viofunctional supramolecular hydrogels, Langmuir, 27(2):529-37 (2011).
Bonte and Juliano, "Interactions of liposomes with serum proteins", Chem Phys Lipids, 40:359-72 (1986).
Browne, et al., "Clinical outcome of autologous chondrocyte implantation at 5 years in US subjects", Clin Orthop Relat Res., 436:237-45 (2005).
Burns, et al., „Physical characterization and lipase suspectibility of short chain lecithin/triglycer mixed micelles potential lipoprotein models, J Biol Chem., 256(6):2716-22 (1981).
Casuso, et al., "Converting drugs into gelators: supramolecular hydrogels from N-acetyl-L-cysteine and coinage-metal salts", Org Biomol Chem., 8:5455-8 (2010).
Choi, et al., "Studies on gelatin-based sponges. Part III: A comparative study of cross-linked gelatin/alginate, gelatin/hyaluronate and chitosan/hyaluronate sponges and their application as a wound dressing in full-thickness skin defect of rat", J Materials Sci., 12:67-73 (2001).
Donati, et al.,"Synergistic effects im semidilute mixed solutions of alginate and lactose-midified chitosam (chitlac)". Biomacromolecules, 8:957-62 (2007).
European Search Report for EP 11827647 dated Jul. 16, 2014.
Gopinath, et al., "Ascorbyl palmitate vesicles (aspasomes): formation characterization and applications", Intl J Pharma., 271(1-2):95-113 (2004).
Hunziker, "Articular cartilage repair: basic science and clinical progress. A review of the current status and prospects", Osteoarthritis Cartilage, 10:432-63 (2002).
International Search Report for PCT/US2011/053075 dated Apr. 17, 2012.
International Search Report for PCT/US2016/031614 dated Jul. 26, 2017.
International Search Report for PCT/US2016/056070 dated Jan. 12, 2017.
International Search Report for PCT/US2017/031615 dated Sep. 25, 2017.

(56) References Cited

OTHER PUBLICATIONS

Kitagawa, et al., "Cationic Vesicles Consisting of 1,2-Dioleoyl-3-Trimethylammonium Propane (DOTAP) and Phosphatidylcholines and Their Interaction with Erythrocyte Membrane", Chem Pharma Bull., 52(4):451-3 (2004).
Magnussen, et al., "Treatment of focal articular cartilage defects in the knee: a systematic review", Clin Orthop Relat Res, 466:952-96 (2008).
Marsich, et al., "Alginate/lactose-modified chitosan hydrogels: A bioactive biomaterial for chondrocyte encapsulation", J Biomat Mater Res A, 84(2):364-76 (2008).
Moliner, et al., "PFGSE-NMR study of the self-diffusiom of sucrose fatty acid monoesters in water", J Colloid Interface Sci., 286(1):360-8 (2005).
Nishimura, et al., "Analysis of reducing end-groups produced by enzymatic scission of glycoside linkages in O-methylcellulose", Carbohydrate Res., 267:291-8 (1995).
Palma, et al., "Evaluation of the surfactant properties of ascorbyl palmitage sodium salt, Eu J Pharma Sci., 16(1-2):37-43 (2002).
Pietzyk, et al., "Degradation of phosphatidylcholine in liposomes containing carboplatin in dependence on composition and storage conditions", Intl J Pharma., 196(2):215-8 (2008).
Preliminary Report on Patentability for PCT/US2011/053075 dated Mar. 26, 2013.
Rajabalaya, et al., "Studies on effect of plasticizer on invitro release and exvivo permeation from eudragit e100 based chlorpheniramine maleate matrix type transdermal delivery system", J Excipients Food Chem., 1(2):1-12 (2010).
SCOGS, substances list, http://www.fda.gov/Food/IngredientsPackagingLabeling/GRAS/SCOGS/ucm084104. Retrieved from interner Apr. 3, 2014.
Szuts, et al., "Study of thermo-sensitive gel-forming properties of sucrose stearates, J Excipients Food Chem., 1(2):13-20 (2010).
Tomsic, et al., "Internally self-assembled thermoreversible gelling mulsions:ISAsomes in methylcellulose, k-carragrrnan, and mixed hydrogels", Langmuir, 25:9525 (2009).
Troung, et al., "Self assembled gels for biomedical applications", Focus Rev., 6:30-42 (2011).
Ullrich, et al.. "Sucrose ester nanodispersions: microciscosity and viscoelastic properties", Eu J Pharma Biopharma, 70:550-5 (2008).
Van Esch, et al., "New functional materials based om self-assembling organogels: from serendipity towards design", Angew Chem Int., 39:2263-66 (2000).
Vohra, et al., "Nanolipi carrier-based thermoreversible gel for localized delivery of docetaxel to breast cancer", Cancer Nanotechnol., 4(1-3):1-12 (2013).
Zhang, et al., "An inflammation-targeting hydrogel for local drug delivery in inflammatory bowel disease", Sci Transl Med., 7(300):300ra128 (2015).
Zhang, et al., "Self-assembled networks and molecular gels derived fro, long-chain, naturally-occurring fatty acids", J Brazilian Chem Soc., 239-55 (2016).
International Search Report PCTUS2019/025782 dated Jun. 26, 2019.
THOUGHCO., "Phosphate-Buffered Saline or PBS Solution", https://www.thoghtco.com/phophate-buffered-saline-pbs-solution-4061933 (2018).
Valecillo, et al., "A liquid crystal of ascorbyl palmittate used as vaccine platform, provides sustained release of anitgen and has instrinsic pro-inflammatory and adjuvant activities which are dependent on MyD88 adaptor protein", Journal of Controlled Release, 214:12-22 (2015).
Bell, et al., "Self-assembling peptides as injectable lubricants for osteoarthritis", Journal of Biomedical Materials Research, 78A(2):236-246 (2006).
International Search Report for PCT application PCT/US2018/016835 dated Jul. 12, 2018.
International Search Report for PCT application PCT/US2018/031654 dated Aug. 8, 2018.

Karim, et al., "Effectiveness and Safety of Tenofovir Gel, and Antiretroviral Microbicide, for the Prevention of HIV Infection in Women", Science, 329:1168-1174 (2010).
Li, et al., Thermosensitive hydrogel of hydrophobically-modified methylcellulose for intravaginal drug delivery, J. Mater. Sci.: Mater. Med., 23:1913-1919 (2012).
Mahalingam, et al., "Design of a Semisolid Vaginal Microbicide Gel by Relating Composition to Properties and Performance", Pharm. Res., 27:2478-2491 (2010).
Vinson, et al., "Direct imaging of surfactant micelles, vesicles, discs, and ripple phase structures by cryo-transmission electron microscopy", Journal of Colloid and Interface Science, 142(1):74-91 (1991).
Zidan, et al., "Maximized Mucoadhesion and Skin Permeation of Anti-AIDS-Loaded Niosomal Gels", Pharmaceutics, Drug Delivery and Pharmaceutical Technology, 103:952-964 (2014).
Baumgart, et al., "Rescue therapy with tacrolimus is effective in patients with severe and refractory inflammatory bowel disease", Aliment. Pharmacol. Ther., 17(10):1273-1281 (Year: 2003).
Estroff, et al., "Water Gelation by Small Organic Molecules", Chem Rev., 104(3): 1201-1217 (2004).
Jibry, et al., "Amphiphilogels as drug carriers: effects of drug incorporation on the gel and on the active drug", Journal of Pharmacy and Pharmacology, 58(2):187-194 (2006).
Kameta, et al., "One-Dimensional Hollow Cylinder and Three-Dimensional Meshworls of supramolecular Nanotube Hyrdogels for Fixation of Proteins", Nanotechnology, 515-519 (2010).
Li, et al., "Role of interleukin-22 in inflammatory bowel disease", World J. Gastroenterol., 20(48): 18177-18188 (2014).
Brodie et al., "The fate of acetanilide in man," Journal of Pharmacology and Experimental Therapeutics, Sep. 1948, 94(1):29-38.
Burke et al., "Hydroxylated aromatic inhibitors of HIV-1 integrase," Journal of Medicinal Chemistry, Oct. 1995, 38(21):4171-8.
Christenson et al., "Enzymatic degradation of poly (ether urethane) and poly (carbonate urethane) by cholesterol esterase," Biomaterials, Jul. 1, 2006, 27(21):3920-6.
Curran et al., "Matrix metalloproteinases: molecular aspects of their roles in tumour invasion and metastasis," European Journal of cancer. Aug. 1, 2000 ;36(13):1621-30.
Dahll et al., "Photocytotoxicity of curcumin," Photochemistry' and Photobiology, Mar. 1994, 59(3):290-4.
Duvoix et al., "Chemopreventive and therapeutic effects of curcumin," Cancer Letters, Jun. Jun. 8, 2005;223(2):181-90.
Hehre, "Ab initio molecular orbital theory7," Accounts of Chemical Research, Nov. 1, 1976, 9(11):3 99-406.
Hergenhahn et al., "The chemopreventive compound curcumin is an efficient inhibitor of Epstein-Barr virus BZLF1 transcription in Raji DR-LUC cells," Molecular Carcinogenesis: Published in cooperation with the University of Texas MD Anderson Cancer Center, Mar. 2002, 33(3): 137-45.
Jahagirdar et al., "Multipotent adult progenitor cell and stem cell plasticity," Stem Cell Reviews, Jan. 2005, 1(1):53-9.
John et al., "Enzymatically Derived Sugar-Containing Self-Assembled Organogels with Nanostructured Morphologsies," Angew. Chem. Int. Ed. 45:4772-4775, 2006.
Kamath et al., "Biodegradable hydrogels in drug delivery," Advanced Drug Delivery Reviews, Jul. 1, 1993, 11(1-2):59-84.
Khopde et al., "Effect of Solvent on the Excited-state Photophysical Properties of Curcumin," Photochemistry and Photobiology, Nov. 2000, 72(5):625-31.
Mazumder et al., "Inhibition of human immunodeficiency virus type-1 integrase by curcumin," Biochemical Pharmacology, Apr. 18, 1995, 49(8):1165-70.
Naumov et al., "The monoclinic form of acetaminophen at 150K," Acta Crystallographies Section C: Crystal Structure Communications, May 15, 1998, 54(5): 653-5.
Peppas et al., "Dynamically swelling hydrogels in controlled release applications," Hydrogels in Medicine and Pharmacy, 1987, 3:109-36.
Pini et al., "The antinociceptive action of paracetamol is associated with changes in the serotonergic system in the rat brain," European Journal of Pharmacology, Jul. 11, 1996, 308(1):31-40.

(56) References Cited

OTHER PUBLICATIONS

Shim et al., "Irreversible inhibition of CD13/aminopeptidase N by the anti angiogenic agent curcumin," Chemistry & Biology, Aug. 1, 2003, 10(8):695-704.

Sui et al., "Inhibition of the HIV-1 and HIV-2 proteases by curcumin and curcumin boron complexes," Bioorganic & Medicinal Chemistry, Dec. 1, 1993, 1(6):415-22.

Tang et al., "Study on the supramolecular interaction of curcumin and β-cyclodextrin by spectrophotometry and its analytical application," Journal of Agricultural and Food Chemistry, Mar. 13, 2002, 50(6):1355-61.

Trouet et al., "Extracellularly tumor-activated prodrugs for the selective chemotherapy of cancer: application to doxorubicin and preliminary in vitro and in vivo studies", Cancer Res., 61: 2843-2846 (2001).

Wang et al., "Hydrogels as Separation Agents. Responsive Gels: Volume Transitions II," Advances in Polymer Science, 67-79 (1993).

\* cited by examiner

REAGENTS AND CONDITIONS: (i) DODECANOIC ACID, DICYCLOHEXYLCARBODIIMIDE (DCC), DIMETHYLAMINOPYRIDINE (DMAP), ANHYDROUS TETRAHYDROFURAN (THF), rt, 24 HRS. (ii) α,ω-DICARBOXYLIC ACID (0.5 EQUI.), DCC, DMAP, DRY THF, rt, 48 HRS. (iii) α,ω-DICARBOXYLIC ACID (1.2 EQUI.), DCC, DMAP, DRY THF, rt, 24 hrs. (iv) 6-BROMOMETHYLHEXANOATE, $K_2CO_3$, DRY THF, REFLUX, 12 hrs. (v) NaOH, MeOH, rt, 12 hrs.

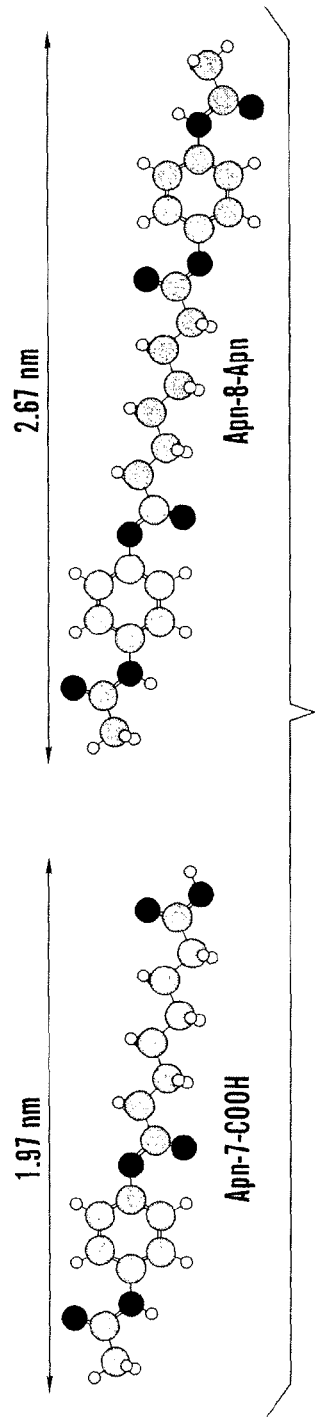
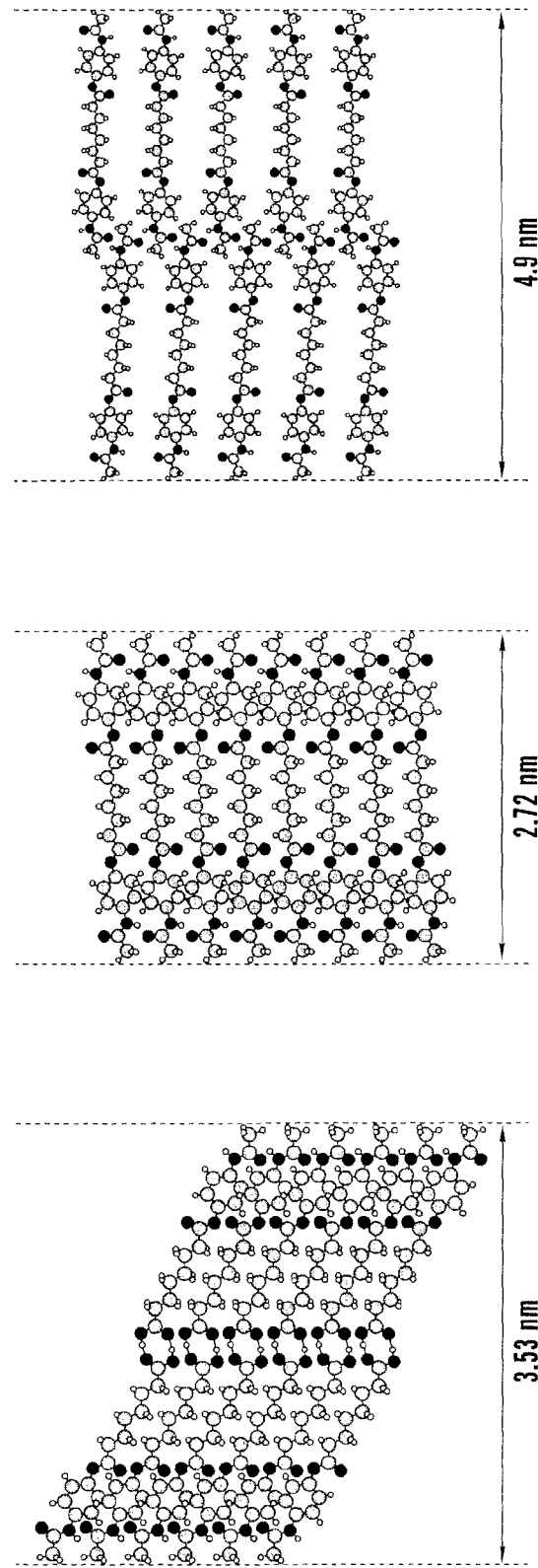
FIG. 4A
FIG. 4B
FIG. 4C
FIG. 4D

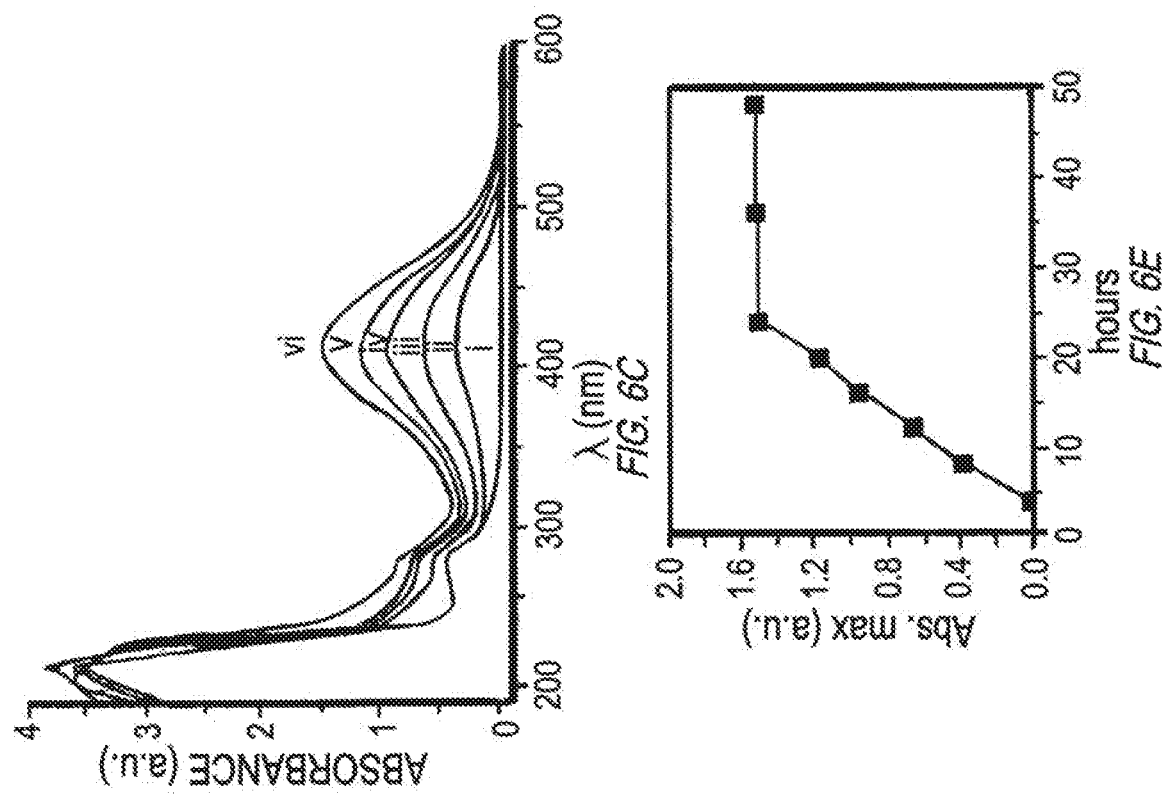
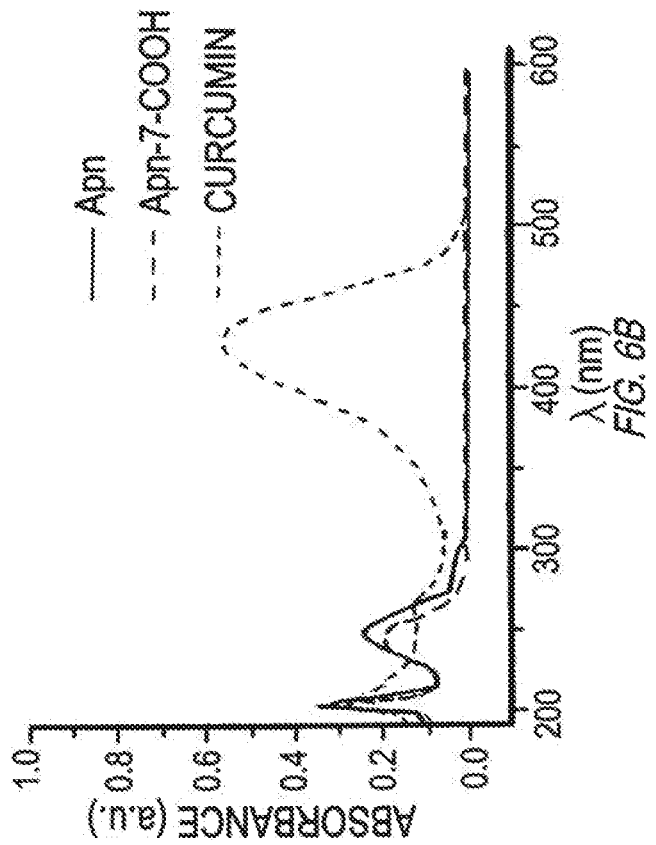
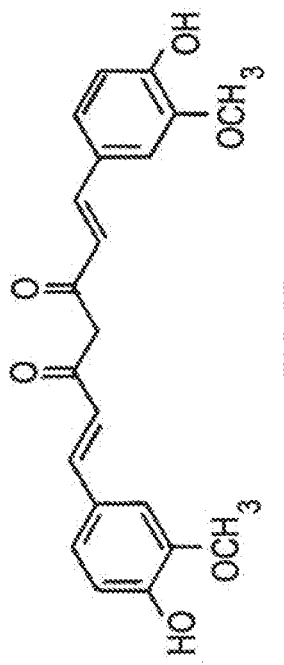
FIG. 6B
FIG. 6C
FIG. 6D
FIG. 6E

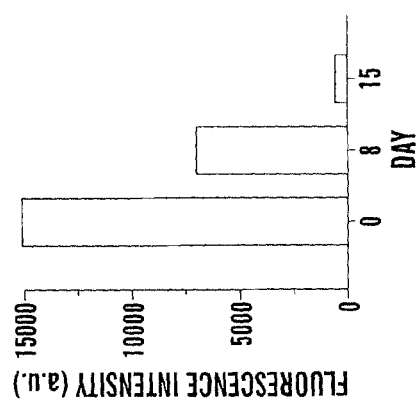
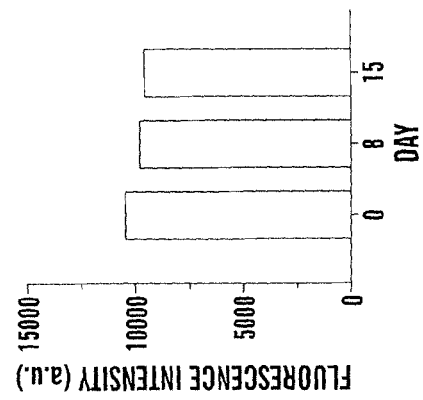
FIG. 13A
FIG. 13B

DRUG DELIVERY COMPOSITION COMPRISING A SELF-ASSEMBLED GELATOR

RELATED APPLICATIONS

This application claims the benefit of priority to U.S. Provisional Patent Application Ser. No. 61/097,565, filed Sep. 17, 2008, the contents of which are incorporated by reference herein in their entirety.

FIELD OF THE INVENTION

This application claims the benefit This invention relates to low-molecular-weight amphiphilic gelators which self-assemble into various nano- and micro-structures in a wide range of organic and aqueous solvents. The gelators have the capability to delivery drugs.

BACKGROUND

A hydro- or organo gel consists of self-assembled macromolecular networks with a liquid filling the interstitial space of the network. The network holds the liquid in place through its interaction forces and so gives the gel solidity and coherence, but the gel is also wet and soft and capable of undergoing some extent of deformation. The gel state is neither solid nor liquid but has some features of both. Self-assembly has been used to develop molecularly defined and functional materials, including hydrogels.

Self-assembled hydrogels can be formulated in a variety of physical forms, including microparticles, nanoparticles, coatings and films. As a result, hydrogels are commonly used in clinical practice and experimental medicine for a wide range of applications, including tissue engineering and regenerative medicine, diagnostics, cellular immobilization, separation of biomolecules or cells and barrier materials to regulate biological adhesions. Hydrogels are appealing for biological applications because of their high water content and biocompatibility. In the last few decades hydrogels have gained considerable attention, and significant progress has been made in designing, synthesizing and using these materials for several biomedical applications including drug delivery. Recent developments include the design and synthesis of novel hydrogels and their use in tissue engineering, drug delivery and bionanotechnology.

Design and synthesis of low-molecular-weight hydrogelators has received considerable attention in soft materials research in terms of its potential use in cosmetics, toiletries and pharmaceutical formulations. Literature study reveals that there are only limited reports on easily achievable and efficient low-molecular-weight gelators that are able to gel water or even water mixtures with other solvents. These hydrogelators are often achieved by multi-step chemical syntheses. See Menger, F. M. & Caran, K. L. (2000) *J. Am. Chem. Soc.* 122, 11679-11691; Sreenivasachary, N. & Lehn, J.-M. (2005) *Proc. Natl. Acad. Sci. USA* 102, 5938-5943; Makarević, J., Jokić, M., Perčić, B., Tomišić, V., Krojić-Prodić, B. & inić, M. (2001) *Chem. Eur. J.* 7, 3328-3341; Oda, R., Huc, I. & Candau, S. J. (1998) *Angew. Chem. Int. Ed.* 37, 2689-2691; Estroff, L. A. & Hamilton, A. D. (2000) *Angew. Chem. Int. Ed.* 39, 3447-3450; Kobayashi, H., Friggeri, A., Koumoto, K., Amaike, M., Shinkai, S. & Reinhoudt, D. N. (2002) *Org. Lett.* 4, 1423-1426; Luboradzki, R., Gronwald, O., Ikeda, M., Shinkai, S. & Reinhoudt, D. N. (2000) *Tetrahedron* 56, 9595-9599; Jung, J. H., John, G., Masuda, M., Yoshida, K., Shinkai, S. & Shimizu, T. (2001) *Langmuir* 17, 7229-7232; and Wang, G. & Hamilton, A. D. (2003) *Chem. Commun.* 310-311.

Low molecular weight gelators are attractive alternatives to their polymeric counterparts as such molecules can be systematically altered and explain various factors which are responsible for the gelation at microscopic level. Because of their importance as scaffolds for various biomaterials design, it is useful to develop low-molecular-weight gelators that ensure strong gelation of water under ambient conditions.

Synthesizing hydrogelators in high quantities is often limited with multiple-step synthesis and poor yields, which make industrial scale production difficult. To develop hydrogelators in large scales, one needs to minimize the number of steps in the synthesis and reduce the side products. Many reported hydrogelators require multiple steps and an elaborated purification process, and many others require costly starting materials and expensive reagents.

Thus, there exists a need in the art for an improved gelator that is easily prepared and can be effectively used for drug delivery. This invention answers that need.

An additional problem in drug delivery is striking a balance between toxicity and therapeutic effect. Hydrogels have been widely applied as carriers in controlled drug delivery systems. See *Hydrogels in Medicine and Pharmacy* (Ed: Peppas, N.) CRC, Boca Raton, Fla. 1987; Peppas, N. A.; Bures, P.; Leobandung, W.; Ichikawa, H. *Eur. J. Pharm. Biopharm.* 2000, 50, 27-46; Peppas, N. *Curr. Opin. Colloid Interface Sci.* 1997, 2, 531-537; Gupta, P.; Vermani, K.; Garg, S. *Drug Discovery Today* 2002, 7, 569-579; Miyata, T.; Uragami, T.; Nakamae, K. *Adv. Drug Deliv. Rev.* 2002, 54, 79-98; Qiu, Y.; Park, K. *Adv. Drug Deliv. Rev.* 2001, 53, 321-339; and Kamath, K.; Park, K. *Adv. Drug Deliv. Rev.* 1993, 11, 59-84. However, many of the systems are derived from polymeric hydrogels as opposed to hydrogels formed through self-assembly of low-molecular-weight gelators (LMWGs). This could be due to the relatively complex synthesis of LMWGs and concerns about possible toxicity of in situ generated fragments from the degradation of LMWGs. Additionally, self-assembled hydrogel-based drug delivery has been hindered by the unknown fate of the host gelator after the gel degradation.

Potential problems can arise relating to the quantity of drug that can be encapsulated within hydrogels, and respective encapsulation efficiency may limit the potential dose or release kinetics that can be achieved. Additionally, polymer-based drug delivery devices that utilize entrapped drug have been known to exhibit an undesired burst release. See Huang, X.; Brazel, C. S. *J. Controlled Release* 2001, 73, 121-136.

In an attempt to address these problems, small molecule drugs have been incorporated into the backbone of polymers. See Bryers, J. D.; Jarvis, R. A.; Lebo, J.; Prudencio, A.; Kyriakides, T. R.; Uhrich, K. *Biomaterials* 2006, 27, 5039-5048; Erdmann, L.; Macedo, B.; Uhrich, K. E. *Biomaterials* 2000, 21, 2507-2512; and Harten, R. D.; Svach, D. J.; Schmeltzer, R.; Uhrich, K. E. *J. Biomed. Mater. Res-A* 2005, 72A, 354-362. However, polymer degradation can lead to polymer fragments with heterogeneous chain lengths that may generate potential toxicity, unwanted side effects, or uncontrollable drug bioavailability.

While progress in this field has been made (see Vemula, P. K.; Li, J.; John, G. *J. Am. Chem. Soc.* 2006, 125, 8932-8938), there is an ongoing need to develop degradable prodrug-based self-assembled gelators that can overcome these problems. This invention also answers that need.

SUMMARY OF THE INVENTION

One embodiment of this invention relates to drug-delivery compositions. The drug may be delivered in various different ways. The drug-delivery composition may be a drug-derived gelator capable of self assembly, where the drug to be delivered is in the backbone of the gelator and released upon degradation of the gelator. One or more agents can be encapsulated in the self-assembled gels. Degradation of the gelator can release both the encapsulated drugs and the drug in the backbone of the gelator. In this aspect, the drug-delivery composition is a multi-drug delivery composition. The composition may also be a self-assembled gelator that is not drug derived but still contains one or more drugs encapsulated in the gelator that can be released upon degradation of the gelator. Prodrug-derived compounds, such as prodrug-derived self-assembled gelators may also be used.

Another embodiment of this invention relates to a single-step method of making a low molecular weight, amphiphilic prodrug or gelator. Prodrugs may be prepared by esterifying a compound having groups capable of promoting self assembly, such as a phenol ring and/or a terminal hydroxyl group, with a dicarboxylic acid to form a prodrug having an ester functionality. Other prodrugs may be prepared by esterifying a compound having a saccharide group, phenol ring, and a primary hydroxyl group with a vinyl ester of a carboxylic acid. Gelators may be prepared by reacting a tris-hydroxyl methyl amine, such as tris, with a fatty acid or methyl ester to form a gelator having an amide functionality.

Another embodiment of this invention relates to methods of drug delivery. A drug may be delivered to a patient by administering the patient a drug-derived or prodrug-derived gelator capable of self assembly, the gelator containing the drug or prodrug in its backbone, a hydrophobic or hydrophilic moiety, and a degradable link between the drug and the moiety. When contacted with an enzyme under physiological conditions, the degradable link cleaves, releasing the drug in the patient. Hydrolytic cleavage under basic conditions can also be used. If the gelator contains an agent, such as another drug, that drug can also be released upon cleavage of the link. A drug may also be administered by encapsulating the drug in a self-assembled gelator, where the gelator may contain an amide functionality and hydrophobic moiety. When contacted with an enzyme under physiological conditions, the amide bond is cleaved, releasing the encapsulated drug.

BRIEF DESCRIPTION OF THE DRAWINGS

FIG. 4A depicts optimized geometries of hydrogelators (4A). FIGS. 4B, 4C, and 4D are schematics of proposed modes of self-assembly into fiber based hydrogels made of Apn-7-COOH (4B), and Apn-8-Apn (4C and 4D).

FIG. 6B shows absorbance spectra for methanolic solution of hydrogelators and curcumin. FIG. 6C shows absorbance spectra of curcumin released from degradation of Apn-7-COOH hydrogel at different time points, i) 4, ii) 8, iii) 12, iv) 16, v) 20 and vi) 24 hrs (after 24 hrs absorbance did not increase). FIG. 6D shows the chemical structure of curcumin. FIG. 6E shows absorbance maxima of curcumin over time.

FIGS. 13A and 13B depict bar graphs showing normalized fluorescence intensity of encapsulated dye within the fibers (13A) in the absence, and (13B) in the presence of synovial fluid that was collected from inflamed human arthritis joints.

DETAILED DESCRIPTION

Drug-Delivery Compositions

Figure 1:
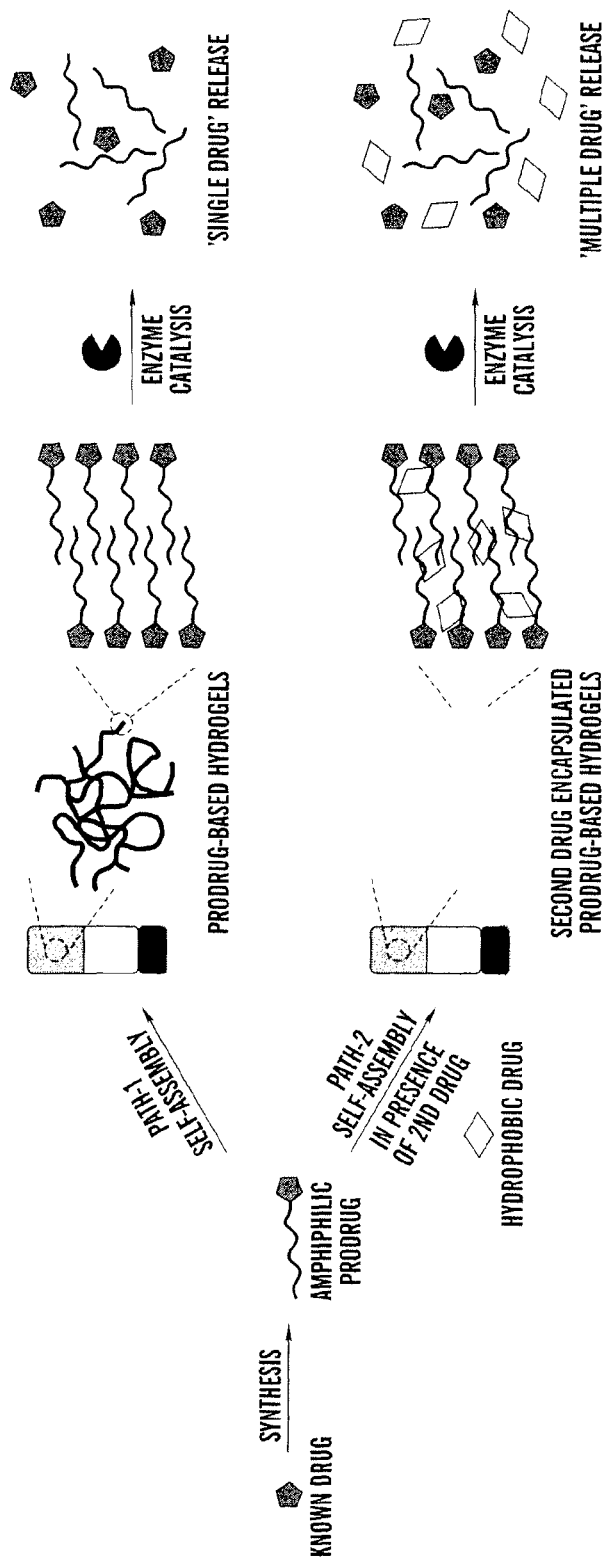
FIG. 1 is a schematic representation of preparing degradable prodrug-based hydrogelators, encapsulation of hydrophobic drug in the gel, and subsequent enzyme triggered single (path-1) and multiple (path-2) drug delivery.

This invention relates to a drug-delivery composition comprising a drug-derived gelator capable of self assembly. After the drug-derived gelator has undergone self assembly, the gelator becomes a self-assembled gelator. The drug to be delivered is part of the backbone of the gelator and can be released upon enzyme-mediated degradation or through hydrolytic cleavage of the gelator. Alternatively, the drug used in the compound may be a prodrug.

Thus, an embodiment of the invention relates to prodrug-delivery composition comprising a prodrug-derived gelator capable of self assembly where the prodrug to be delivered is part of the backbone of the gelator and can be released under the appropriate conditions, e.g., enzyme-mediated degradation or through hydrolytic cleavage of the gelator. Like the drug-derived gelator, the prodrug-derived gelator becomes a self-assembled gelator upon self assembly. Any drug or prodrug known to those of skill in the art may be used with this invention, provided that the drug or prodrug, and/or gelator is biocompatible with the host that the drug-delivery composition is being administered to.

As used herein, the term "drug" means a molecule, group of molecules, complex or substance administered to an organism for diagnostic, therapeutic, medical or veterinary purposes. Drugs include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics and forensics. In certain embodiments, the drug is hydrophilic. In certain other embodiments, the drug hydrophobic.

As used herein the term "prodrug" means a drug, drug precursor of modified drug that is not fully active or available until converted in vivo or in situ to its therapeutically active or available form.

In addition to containing the drug or prodrug, or a derivative thereof, the backbone of the drug-derived or prodrug-derived gelator may also contain a hydrophobic or hydrophilic moiety, and a degradable link between the drug or prodrug and the moiety. For example, if the drug or pro-drug is hydrophilic then the moiety is hydrophobic and if the drug or pro-drug is hydrophobic then the moiety is hydrophilic. Without wishing to be bound by theory, the having both a hydrophilic component and a hydrophobic component allows the gelator to self-assemble under appropriate conditions. Any degradable link that is cleavable under the required conditions, i.e. a stimuli, can be used. Preferably, the degradable link is cleaved at least 10 times or more, preferably at least 100 times faster under the required conditions or under a first reference condition (which can, e.g., be selected to mimic or represent intracellular conditions) than in the blood of a subject, or under a second reference condition (which can, e.g., be selected to mimic or represent conditions found in the blood or serum).

The stimuli can be of biological origin. As used herein, the term "biological origin" refers to conditions that are present in biological systems. In certain embodiments, the degradable link is cleavable under biological conditions, e.g., conditions present in the blood or serum, or conditions present inside or out side the cell, tissue or organ. The degradable link can be cleavable only under conditions present in a disease state of a cell, tissue or organ, e.g. inflammation. Without wishing to be bound by theory, the link is cleaved when appropriate conditions are present for the cleavage, e.g. pH or concentration. Thus allowing for release of drug at targeted tissue and/or organ. This can allow use of lower dosage because the drug is only released at the required site. Another benefit is lowering of toxicity to other organs and tissues.

Without wishing to be bound by theory, cleavage of the link under biological conditions allows self-titering drug delivery. As used herein, the term "self-titering" refers to release of drug based on the severity of disease or inflammation. By way of explanation, when the severity of disease is severe, stimuli for cleaving the degradable link is high and more drug is released and when severity of disease is low, stimuli is low and less drug is released. Thus, for example, in a strong inflammatory response, there would be more enzymes present and this would lead to higher release of the drug, and when the inflammation subsides, i.e. remission, the drug would not be released.

In certain embodiments of the invention, any degradable link that is cleavable upon contact with an enzyme and/or through hydrolysis can be used. Examples of degradable links include ester, amide, anhydride, and carbamate linkages. Suitable hydrophobic moieties include phenol rings, hydroxyl groups, polymethylene chains, amides, carbonyls, and carboxylic acids.

In certain embodiments, the degradable link can be phosphate based, e.g. phosphodiester. Phosphate-based linking groups are cleaved by agents that degrade or hydrolyze the phosphate group. An example of an agent that cleaves phosphate groups is phosphatases.

In some embodiments, the degradable link can be linking group that is cleaved under acidic conditions. In preferred embodiments acid cleavable linking groups are cleaved in an acidic environment with a pH of about 6.5 or lower (e.g., about 6.0, 5.5, 5.0, 4.5, 4.0 or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, —C(O)O—, or —OC(O)—. Another degradable link that is also susceptible to low pH is disulfide (—S—S—)

A degradable link can be susceptible to temperature, for example cleavable at high temperature, e.g., cleavable in the temperature range of 37-10, 40-100, 45-100, 50-100, 60-100, 70-100° C. For example, the linkage can be cleaved by an increase in temperature.

Other degradable links are redox cleavable and are cleaved upon reduction or oxidation. One reductively degradable link is a disulphide linking group (—S—S—).

In certain embodiments, stimuli can be ultrasound, temperature, pH, metal ions, light, electrical stimuli, electromagnetic stimuli, and combinations thereof.

In certain embodiments, the drug-derived or prodrug-derived gelator comprises a hydrophilic drug and a hydrophobic moiety. In other embodiments, the drug-derived or prodrug-derived gelator comprises a hydrophobic drug and a hydrophilic moiety.

The gelator can either be a hydrogelator or organogelator. Hydrogels, as known to those of skill in the art, are 3-D networks of molecules typically covalently or ionically linked together where water is the major component (usually greater than 80%). Gels can be formed via self-assembly of gelators or via chemical crosslinking of gelators. Water-based gelators can be used to form hydrogels, whereas organogelators are gelators that form gels (oganogels) in organic solvents. In one embodiment, the gelator is the esterification reaction product of the drug or prodrug and a $C_{1-22}$ carboxylic acid. Preferably, the carboxylic acid is a dicarboxylic acid. The carboxylic acid may contain saturated or unsaturated hydrocarbon chains.

Any drug or prodrug that is capable of undergoing self assembly may be used as the drug or prodrug in the drug-derived or prodrug-derived gelator. In one embodiment, the drug or prodrug is capable of undergoing self assembly upon esterification with a fatty acid or dicarboxylic acid. The self-assembled gelator may be a single-component gelator that does not require any other complementary molecules or base salts to induce self assembly.

Preferably, the drug or prodrug used in the gelator is easily functionalizable without compromising the base structure of the drug. Functionalizable groups include hydroxyls, amines, carboxylic acids, thiols, anhydrides, and others known to one of skill in the art. Either the drug or the group that is conjugated to the drug may have particular moieties that can be used to induce self-assembly. In general, phenol rings, hydroxyl groups, polymethylene chains, amides, carbonyls, or carboxylic acids may be used to aid in the self-assembly process. For instance, the drug used in the gelator may contain a phenol ring and a terminal hydroxyl group. The drug may also contain other functional groups that promote self assembly, in particular self assembly that occurs upon esterification with a fatty acid or dicarboxylic acid.

There are different ways to promote self assembly. The functional groups of the gelator and/or drugs can promote self assembly by facilitating the ability of the gelator to interact non-covalently with other gelator molecules, for instance by facilitating hydrogen bonding, intermolecular interactions through pi-pi stacking, and/or molecular association through van der Waals interactions.

The other significant parameter that promotes self-assembly is the solubility of the gelator, where the solubility properties of gelators can play a significant role in determining gelation efficiency. As known to those of skill in the art, self-assembly is typically driven by a stimulus that alters the solubility of the gelator. A change in solubility can be induced by a variety of techniques known to those of skill in the art, including changing the temperature of the solvent/gelator mixture. The solubility properties of many different drugs can thus be modulated by appropriate functionalization with various moieties to tailor the solubility and self-assembling properties.

Various methods and techniques can be used to achieve dissolution of gelators/prodrug/amphiphile in aqueous solution or organic solvents, including altering the temperature, sonication, grinding, co-solvent method, mixed solvent method, and combinations thereof. For example, a drug that is soluble in water may be resistant to induce self-assembly in water. A hydrophobic tail, for instance a polymethylene chain, could be added to the drug. Most hydrophobic tails will not be soluble in water at room temperature, yet will solubilize when the water is heated. When the composition cools, the gelator precipitates in a highly organized self-assembled fashion. These techniques can be used for hydrogelator and organogelators alike, particularly in instances where it is desirable that the gelator initially not be soluble in a particular solvent.

Others methods may also be used to modify solubility. For example, certain prodrugs may dissolve in a solvent like DMSO but not water. In this instance, the prodrug could first be dissolved in DMSO, or any other water-miscible solvent, then placed into water (a non-solvent for the prodrug). Because DMSO is miscible with the water, the prodrug will become supersaturated and precipitate into a highly organized self-assembled state. In these type of scenarios, the alterations to the drug would not be temperature dependent, as discussed above, but may be used just as effectively to increase solubility in one solvent and not in another.

Using these various techniques and methods to achieve self-assembly enables self assembly to occur in vitro or in situ. For instance, injecting the gelator into warm solution and as it cools (typically to 37° C.) would promote self assembly. Alternatively, the gelator could be injected with a suitable water-miscible solvent and as this solvent mixes with water in the tissue, the gelator would self assemble. Thus, injectable or implantable methods and techniques can also be used to promote self assembly of the gelator.

The drug-based gelators and prodrug-based gelators of this invention can be based on various drugs or prodrugs known to those of skill in the art. The drug used in the gelator preferably contains a phenol group and a terminal hydroxyl group. More preferably, the drug is acetaminophen or a derivative of acetaminophen, and the gelator is an acetaminophen-derived gelator. Most preferably, the acetaminophen-derived gelator is selected from formula (I) or formula (II):

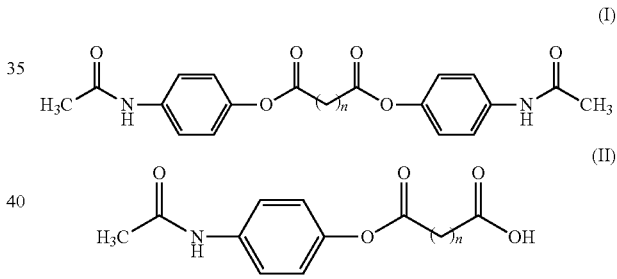

wherein n in each formula represents an integer from 1-22. Preferably n is 1-12 in both formula (I) and formula (II), with 6-12 being the most preferred range of n.

The prodrug, while similar to the drug, preferably contains a phenol group, a terminal hydroxyl group, such as hydroxymethyl group, and a saccharide or a saccharide derivative such as poly-saccharide. In a preferred embodiment, the prodrug is salicin or a derivative of salicin and the gelator is a salicin-derived gelator. Most preferably, the prodrug-derived gelator is of formula (III):

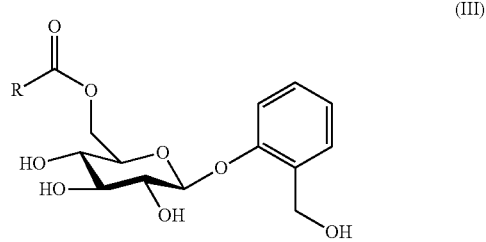

where R is a saturated or unsaturated $C_{1-21}$ alkyl group.

The drug-delivery composition may also contain an agent encapsulated in the self-assembled gels that can be released with the drug or prodrug upon enzyme-mediated degradation or hydrolytic cleavage of the gelator. Suitable agents include organic dyes, vitamins, derivatives of vitamins, peptides, proteins, enzymes, RNAi, chemotherapeutics, anti-inflammatory drugs, and combinations thereof. Preferably, the agent is another drug, an enzyme, or both an enzyme and another drug.

When one or more drugs are encapsulated in the gelator, the drug-delivery composition is capable of delivery two or more drugs through the composition. Thus, an embodiment of the invention relates to a multi-drug delivery composition that contains a self-assembled gelator containing a first drug or prodrug and a second drug. The first drug or prodrug, as described above, can be part of the backbone of the gelator and the second drug can be encapsulated in the gel of the gelator. Upon exposure to a suitable enzyme or upon hydrolytic cleavage of the gelator, the first drug and the second drug can be simultaneously or nearly simultaneously released. It is also possible for the composition to further contain one or more additional drugs in the backbone of the gelator and/or one or more additional drugs encapsulated in the gel of the gelator.

In a preferred embodiment, the first drug is an analgesic or antipyretic drug and the second drug is an anti-inflammatory agent, or vice versa. The two drugs may be complementary to one another. For instance, both drugs may be designed to treat the same ailment or both drugs may be routinely prescribed by a physician to treat different aspects of the same ailment. Both drugs may be delivered in a sustained release. When the drug is a hydrophobic drug, it can be encapsulated in the hydrophobic pockets of the self-assembled gelator, making for particularly effective encapsulation.

Drugs may also be delivered through a self-assembled gelator when the composition is not derived from a drug or prodrug. This embodiment of the invention relates to a drug-delivery composition that contains a drug and a self-assembled gelator having an ester, amide, or carbamate functionality and a hydrophobic moiety in the backbone of the gelator. The drug is encapsulated in the gel and can be released upon enzyme-mediated degradation of the gelator or hydrolytic cleavage of the gelator.

In a preferred embodiment, the gelator is a tris-based hydrogelator having an amide functionality. Exemplary gelators are those of formula (IV):

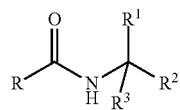

(IV)

wherein R is a saturated or unsaturated $C_{1-22}$ alkyl group, and $R^1$, $R^2$, and $R^3$ each independently represent a hydroxyalkyl group, such as a hydroxy $C_{1-6}$ alkyl. Preferably, R is a saturated or unsaturated $C_{9-21}$ alkyl group (more preferably $C_{12-16}$), and $R^1$, $R^2$, and $R^3$ each represent a hydroxymethyl group. More preferably, the gelator is the reaction product of 2-amino-2-hydroxymethylpropane-1,3-diol (tris) and a fatty acid or methyl ester of a fatty acid. Tris, as known to those of skill in the art, is widely used as a component of buffer solutions. In particular, it is useful to act as a buffer to maintain tissue microenvironment pH, typically at a pH between 7-9.

Certain enzymes have been found to be particularly useful for tris-based hydrogelators. For instance, enzymes in the amidase or metalloprotease families of enzymes have been found to be useful at cleaving amide bonds.

Another embodiment of this invention relates to a single-component drug-based gelator composition, where the gelator contains functional groups that exist within the drug and/or within a modified moiety that is conjugated to the drug. The functional groups can interact via pi-pi stacking, hydrophobic interactions, and/or hydrogen bonding. As discussed above, the drug can be released enzymatically and/or hydrolytically.

Compositions of the invention can have a variety of different shapes and structures. For example. The compositions of the invention can be formed into capsules, tablets, films, microspheres or the like. In certain embodiments, the compositions of the invention are particles e.g. nanoparticles or microparticles.

In certain embodiments, the composition is a particle having one dimension in the range of 10,000-100,000 nm. In other embodiments, the composition is a particle having one dimension in the range of 1000-10,000 nm. In certain embodiments, the particles have one dimension in the range of 1-3000 nm.

In some embodiments, the particles have one dimension in the range of 1-1000 nm. Preferably the particles have one dimension in the range of 20-750 nm. More preferably the particles have one dimension in the range of 20-500 nm. And most preferably the particles have one dimension in the range of 50-500 nm.

In certain embodiments, the nano- or micro-particles are a hydrogel comprising prodrug-derived gelator. In certain further embodiments of this and other aspects of the invention, components of the hydrogel are non covalently bound with each other.

As discussed above, drugs can also be encapsulated in the compositions of the invention. In certain embodiments, the drug is indomethacin or ethambutol. In some embodiments, indomethacin or ethambutol is connected to a peptide, fatty acid or sugar moiety.

In some embodiment, the indomethacin is of formula (V):

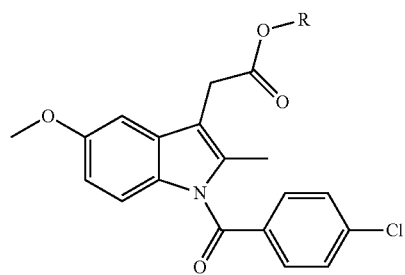

(V)

wherein R is peptide comprising 1-40 amino acids or R is saturated or unsaturated $C_1$-$C_{21}$ alkyl group. In some embodiments, R is $C_1$-$C_6$ alkyl. In some other embodiments, R is $C_6$-$C_{12}$ alkyl.

In some embodiments, the ethambutol is of formula (VI):

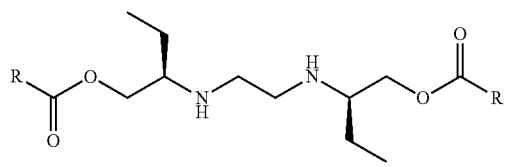

wherein R is a peptide comprising 1-40 amino acids or R is saturated or unsaturated $C_{1-21}$ alkyl group. In some embodiments, R is $C_1$-$C_6$ alkyl. In some other embodiments, R is $C_6$-$C_{12}$ alkyl.

In certain embodiments, the drug promotes specific cellular function.

In certain embodiments, the encapsulated drug is a small molecule that can promote differentiation, de-differentiation, trans-differentiation, or reprogramming of cells.

The compositions of the invention can comprise two or more different gelators. For example, the two or more different gelators can differ from each other by drug or prodrug, hydrophobic or hydrophilic moieties present in the backbone.

In certain embodiments, the composition comprises two different gelators.

In certain embodiments, hydrogel can by lyophilized. Without wishing to be bound by theory, lyophilized gels can be formulated for aerosol based drug delivery.

It is to be understood that upon release from the composition, drug is released in its therapeutically active form. This applies to both the drugs or prodrugs that are part of the gelator backbones and the drugs that are encapsulated within the gel and are not part of the backbone.

As one of skill in the art can appreciate, the precise amount of drug that is available for release is pre-defined by the composition of the drug or prodrug used in the gelator. Without wishing to be bound by theory, the amount available for release can be increased or decreased by changing the composition of the gelator.

The compositions of the invention are particularly useful, e.g., for improving safety, targeting efficiency, compliance and efficacy for indications benefiting from single-dose, prolonged action or tissue-specific formulations. Exemplary indications include, but are not limited to, allergy (e.g. contact dermatitis), arthritis, asthma, cancer, cardiovascular disease, diabetic ulcers, eczema, infections, inflammation, muscuscitis, periodontal disease, psoriasis, respiratory pathway diseases (e.g., tuberclosis), vascular occlusion, pain.

The compositions of the invention are also useful for oral drug delivery, inner ear drug delivery, transdermal drug delivery (e.g., permeabilization), an anti-bacterial. Furthermore, the compositions can be used to deliver drugs for treatment of pain and graft versus host diseases.

Method of Making Prodrug and Gelator

An embodiment of this invention relates to methods of making prodrugs and gelators. One embodiment relates to a single-step method of making a low molecular weight, amphiphilic prodrug, comprising the step of esterifying a compound having a phenol ring and terminal hydroxyl group with a dicarboxylic acid, for instance a $C_{1-22}$ dicarboxylic acid, to form an amphiphilic prodrug containing an ester functionality. The esterification reaction can take place without the use of a catalyst.

The prodrug may then be used as a gelator, as discussed above. For instance, the amphiphilic prodrug can be contacted with a solvent to induce self assembly to form a prodrug-based gelator. Suitable solvents include water, water containing one or more salts, organic solvents, and oils. Preferred organic solvents include hexane, heptane, benzene, toluene, mesitylene, ethylacetate, chloroform, ethanol, propanol, butanol, tertiary butanol, tetrahydrofuran, acetonitrile, and combinations thereof. Preferred solvent oils include petrol, diesel, gasoline, vegetable oil, cooking oil, polyunsaturated oils, and combinations thereof.

The functional groups of the gelator promote self assembly by facilitating hydrogen bonding, intermolecular interactions through pi-pi stacking, and molecular association through van der Waals interactions, as discussed above. Self assembly may take place in the presence of an encapsulating one or more agents so that the agent or agents are encapsulated in the gel.

Preferably, the compound and the agents are both drugs or prodrugs. More preferably, the compound is acetaminophen, and most preferably, the amphiphilic prodrug is a compound selected from formula (I) or formula (II), discussed above. The reaction typically takes place at about 37-40° C. for about 24-72 hours under continuous agitation.

In certain embodiments, the drug is indomethacin or ethambutol. In some embodiments, indomethacin or ethambutol is connected to a peptide, fatty acid or sugar moiety.

In some other embodiment, the indomethacin is of formula (V).

In yet still other embodiments, the ethambutol is of formula (VI).

Another embodiment relates to a single-step method of making a low molecular weight, amphiphilic gelator, comprising the step of reacting a tris-hydroxyl methyl amine, such as tris, with a fatty acid or methyl ester of a fatty acid to form an amphiphilic gelator having an amide functionality. Suitable fatty acids include fatty acids having a saturated or unsaturated $C_{1-21}$ alkyl group, such as lauric, caprylic, myristic, palmitic, and oleic acid. The reaction can take place without the use of a catalyst. Preferred reaction conditions include having the reaction takes place in dimethylsulfoxide and $K_2CO_3$ at about 20° C. for about 24-48 hours.

As discussed above, the gelator may be contacted with a solvent to induce self assembly. The amphiphilic gelator having an amide functionality is preferably of formula (IV), above.

Another embodiment relates to a single-step method of making a low molecular weight, amphiphilic prodrug, comprising the step of esterifying a compound having a saccharide group, phenol ring and primary hydroxyl group with a vinyl ester of carboxylic acid to form an amphiphilic prodrug containing an ester functionality.

The esterification reaction preferably takes place in presence of a Lipase enzyme, such as lipolase. The reaction typically takes place at about 37-40° C. for about 24-72 hours under continuous agitation. The amphiphilic prodrug is preferably salicin or a salicin derivative, such as that of formula (III), above.

Salicin has generally been considered a prodrug of aspirin. It contains a polysaccharide ring, an aromatic group and hydroxyl group. To prepare the preferred gelator of this embodiment, a hydrophobic polymethylene chain can be reacted with the primary hydroxyl group of the glucose group in the salicin to make the amphiphilic prodrug-based gelator.

Method of Drug Delivery Another embodiment of this invention relates to a method of drug delivery. The method contains a first step of administering to a patient in need thereof a drug-derived or prodrug-derived gelator capable of self assembly. Upon self assembly, the gelator becomes a self-assembled gelator. The backbone of the gelator contains the drug or prodrug, a hydrophobic moiety, and a degradable link between the drug or prodrug and hydrophobic moiety. The second step involves contacting the compound or gelator with an enzyme (in an enzymatic cleavage) or water (in a hydrolytic cleavage) to cleave the degradable link and release the drug or prodrug in the patient.

Preferably, the gelator is an acetaminophen-derived gelator or a salicin-derived gelator, as discussed above. Preferred acetaminophen-derived gelators include gelators selected from formula (I) or formula (II), and preferred salicin-derived gelators include gelators having formula (III), above. The gelator may include one or more drugs encapsulated in the gel of the gelator.

In certain embodiments, the gelator is indomethacin or ethambutol derived hydrogelator. In some embodiments, indomethacin or ethambutol is connected to a peptide, fatty acid or sugar moiety.

In some other embodiment, the indomethacin is of formula (V).

In yet still embodiments, the ethambutol is of formula (VI).

The degradable bond between the drug or prodrug and hydrophobic moiety may be any bond known in the art that is degradable enzymatically or hydrolytically. Bonds capable of being cleaved include ester, amide, anhydride, and carbamate bonds.

When the gelator is contacted with an enzyme under conditions sufficient to cleave the degradable bond, an enzymatic cleavage occurs. Any enzyme capable of cleaving the bond may be used. Suitable enzymes include Lipase enzymes, such as lipolase. The enzyme cleaves the degradable bond in the compound to release the derived drug or prodrug and the fatty acid.

In instances when the gelator contains one or more drugs encapsulated in the self-assembled gel, the enzyme cleaves the degradable bond in the gelator to release the encapsulated drugs, the derived drug or prodrug, and a fatty acid. In this instance, the enzyme cleavage releases the encapsulated drug and derived drug or prodrug simultaneously or nearly simultaneously. Preferably, the enzymatic cleavage takes place under physiological conditions.

As discussed above, the self-assembled gelator may encapsulate one or more drug as well as one or more agents, such as an enzyme, in the gel of the gelator. An embodiment of this invention thus relates to a self-assembled gelator that contains an enzyme, where the encapsulated enzyme cleaves the gelator and releases the drugs. The encapsulated enzyme may be present within the hydrogel during the gelation process, and then be released so that it can cleave the gelator and subsequently release the drug or prodrug. The enzyme may also be an external enzyme, or an enzyme that is otherwise not encapsulated in the gelator.

When the gelator is contacted with water under conditions sufficient to cleave the degradable bond, a hydrolytic cleavage occurs. Similar to the enzymatic cleavage, the hydrolytic cleavage can release the derived drug or prodrug and the fatty acid, or, when the gelator contains one or more encapsulated drugs, the cleavage can release the encapsulated drugs, the derived drug or prodrug, and a fatty acid.

Hydrolytic cleavage often takes place at elevated or basic pH conditions, for instance, at a pH ranging from about 6-12.

The drug is capable of being delivered in a sustained release. Sustained release, as appreciated by those of skill in the art, can delay the release of the drug or prodrug for a desired period of time. Depending on the parameters, the release can be delayed from minutes to days to months or even years, especially when administered under physiological conditions (a pH of about 7.4 and a temperature of about 37° C.). The sustained release can be controlled by the concentration of the enzyme and, if applicable, the body temperature of the patient. For instance, sustained release can be accelerated via high enzyme concentration. In a preferred embodiment, the sustained release is delivered without a burst release, or with only a minimal burst release.

Another embodiment of this invention relates to a method of drug delivery, comprising a first step of administering to a patient in need thereof a drug or prodrug encapsulated in a self-assembled gel. The backbone of the gelator contains an amide functionality and a hydrophobic moiety. The second step involves contacting the gelator with a suitable enzyme to cleave the amide bond in the gelator and release the drug or prodrug in the patient.

Other degradable links besides the amide bond may also be used. In this embodiment, the method of drug delivery contains a first step of administering to a patient in need thereof a drug or prodrug encapsulated in a self-assembled gelator. The backbone of the gelator contains a hydrophobic moiety and a degradable link between the drug or prodrug and the hydrocarbon chain. The second step involves contacting the gelator with a suitable enzyme to cleave the degradable link in the gelator and release the drug or prodrug in the patient. The cleavage takes place under physiological conditions.

Preferably, the gelator is a tris-based amphiphile, for instance the reaction product of 2-amino-2-hydroxymethyl-propane-1,3-diol and a fatty acid or methyl ester. Preferred gelators are of formula (IV), discussed above.

The drugs and prodrugs, whether encapsulated and/or part of the backbone of the gelator, can be administered to a patient that is suffering from an ailment or otherwise in need of such drugs. Typical ailments include as cancer, arthritis, cardiovascular disease, and the like. Materials made from, for instance, salicin or salicin derivatives and acetaminophen or acetaminophen derivatives can be used as anti-inflammatory materials. These drugs and prodrugs can be combined other anti-inflammatory drugs or their prodrugs to treat, for example, various arthritis ailments.

It is possible to administer the drugs or prodrugs through various known delivery techniques, including injection and implantation. Injection and implantation are particularly feasible in view of the ability of the gelator to form in situ (i.e. in situ self-assembly). Injecting or implanting the drug or prodrug composition into a joint together with the sustained-release properties enables the drug to provide a long-term release over a period of time. This is particularly suitable in instances where enzymes that are present in a joint are naturally released upon inflammation of the joint. When the joint becomes inflamed and releases the enzyme, the enzyme, in turn, cleaves the drug or prodrug composition, which releases the anti-inflammatory drugs. After the anti-inflammatory drug is released, the enzyme concentration decreases. The drug or prodrug composition that is not cleaved remains stable until another inflammatory stimulus. This phenomenon can be referred to as "on-demand release," where the level of inflammation regulates the amount and timing of drug/prodrug release.

Compounds It is believed the compounds discussed above as gelators are novel in their own right. Therefore, an additional embodiment of this invention is directed to the following individual compounds, separate from their use as gelators.

One embodiment thus relates to a compound of formula (I):

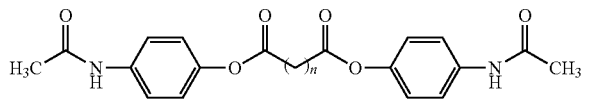

where n represents an integer from 1-22, preferably ranging from 1-12, and more preferably from 6-12.

Another embodiment relates to a compound of formula (II):

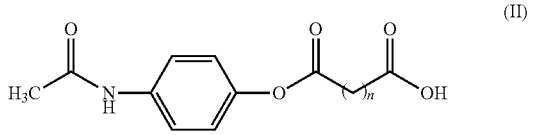

where n represents an integer from 1-22, preferably ranging from 1-12, and more preferably from 6-12.

Another embodiment relates to a compound of formula (III):

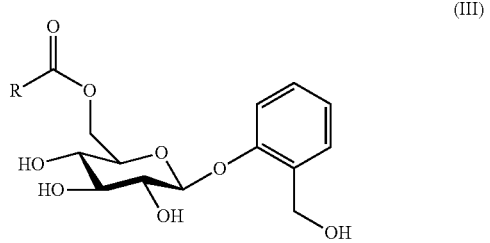

where R is a saturated or unsaturated $C_{1-21}$ alkyl group.

Another embodiment relates to a compound of formula V:

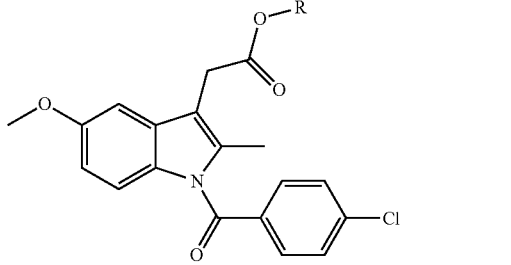

wherein R is peptide comprising 1-40 amino acids or R is saturated or unsaturated $C_1$-$C_{21}$ alkyl group. In some embodiments, R is $C_1$-$C_6$ alkyl. In some other embodiments, R is $C_6$-$C_{12}$ alkyl.

Another embodiment relates to a compound of formula VI:

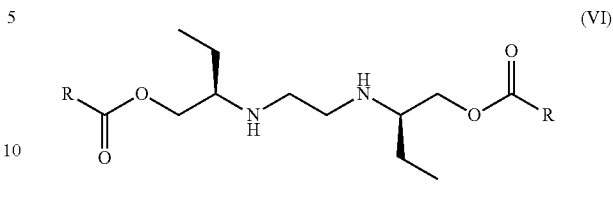

wherein R is a peptide comprising 1-40 amino acids or R is saturated or unsaturated $C_{1-21}$ alkyl group. In some embodiments, R is $C_1$-$C_6$ alkyl. In some other embodiments, R is $C_6$-$C_{12}$ alkyl.

EXAMPLES

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

Example 1

Self-Assembled Acetaminophen Prodrugs

Utilization of enzyme catalysis as a tool to disassemble self-assembled hydrogels to control the release encapsulated drug provides an opportunity to employ a wide range of enzyme-specific low-molecular-weight hydrogelators.

In this example, low-molecular-weight amphiphilic prodrugs are synthesized as hydrogelators from biocompatible fatty acids and a well-known drug, acetaminophen (Apn), (which belongs to a class of drugs called analgesics (pain relievers) and antipyretics (fever reducers)). This reaction was performed in a single-step esterification. The example shows the prodrug's ability to self-assemble into nanoscale structures in aqueous solutions to form hydrogels that may subsequently encapsulate a second drug such as curcumin, which is a known chemopreventive and anti-inflammatory hydrophobic drug. Upon enzyme triggered degradation, the hydrogel can release single or multiple drugs at physiologically simulated conditions in vitro.

Given that the degradation products consist of the drug and a fatty acid, this approach has an advantage over polymer-based prodrugs that generate polymer fragments with heterogeneous chain lengths upon degradation that may present complex toxicity profiles. Additionally, drug release can occur without burst release by an enzyme triggered hydrogel degradation mechanism. Spectrophotometric experiments supported the drug release, and the rate was controlled by modulation of temperature and enzyme concentration. To test the cytocompatibility of amphiphilic prodrugs, and their effect on cell characteristics such as viability, proliferation, adhesion and cell phenotype, a series of experiments was performed with mesenchymal stem cells (MSCs). After treating the MSCs with amphiphilic prodrugs, it was found that the MSCs retain their stem cell properties, including the capacity of multi-lineage differentiation, and maintain their adhesive and proliferation capacities with high viability. Therefore, it is believed that this approach has broad applications as drug delivery vehicles from a wide range of prodrug-based gelators.

The existing ambiguity can be substantially decreased by designing prodrugs-based LMWGs from existing drugs, for instance existing drugs whose metabolic pathways are well studied. Such prodrugs may also encompass functional groups which can promote self-assembly in aqueous solutions, and pose ability to encapsulate drugs within the pockets of hydrogel.

In this example, delivery vehicles are developed for single and multiple drugs. Upon degradation, drug-encapsulated prodrug-based hydrogels can release drug-1 (which generates from cleavage of prodrug) and drug-2 (the encapsulated drug(s)). See the FIG. 1 for schematic representation of single and multiple drug delivery from prodrug based hydrogels.

Drug delivery can occur from hydrogels through various mechanisms such as swelling and dissolution so on. Biodegradability or dissolution may be designed into hydrogels via enzymatic, hydrolytic, or environmental (e.g. pH, temperature, or electric field) pathways. Enzymes, which can permit the release of encapsulated therapeutics in desired locations, can be employed as stimuli for drug release, for instance, in tumors as a result of the enzymatic action of tumor-associated proteases such as plasmin, or in selected sites of the gastro intestinal tract under the influence of digestive enzymes. Enzymes have also been used in biocatalysis as a tool to make the gelators from biomass and as stimuli to degradation of the gel which triggered drug delivery.

In this example, biocompatible amphiphilic prodrugs as LMWGs have been developed to encapsulate hydrophobic drugs and subsequently release single and multiple drugs upon enzyme mediated gel degradation (FIG. 1). The well-known drug N-(4-hydroxyphenyl)acetamide, which is also known as acetaminophen (Apn), was chosen, as its drug activity has been well studied. Apn is a common analgesic and antipyretic drug that is used for the relief of fever, headaches, and other minor aches and pains. It is remarkably safe in recommended doses, and its route of metabolism in human has extensively been investigated and found to be safe.

Figure 2:
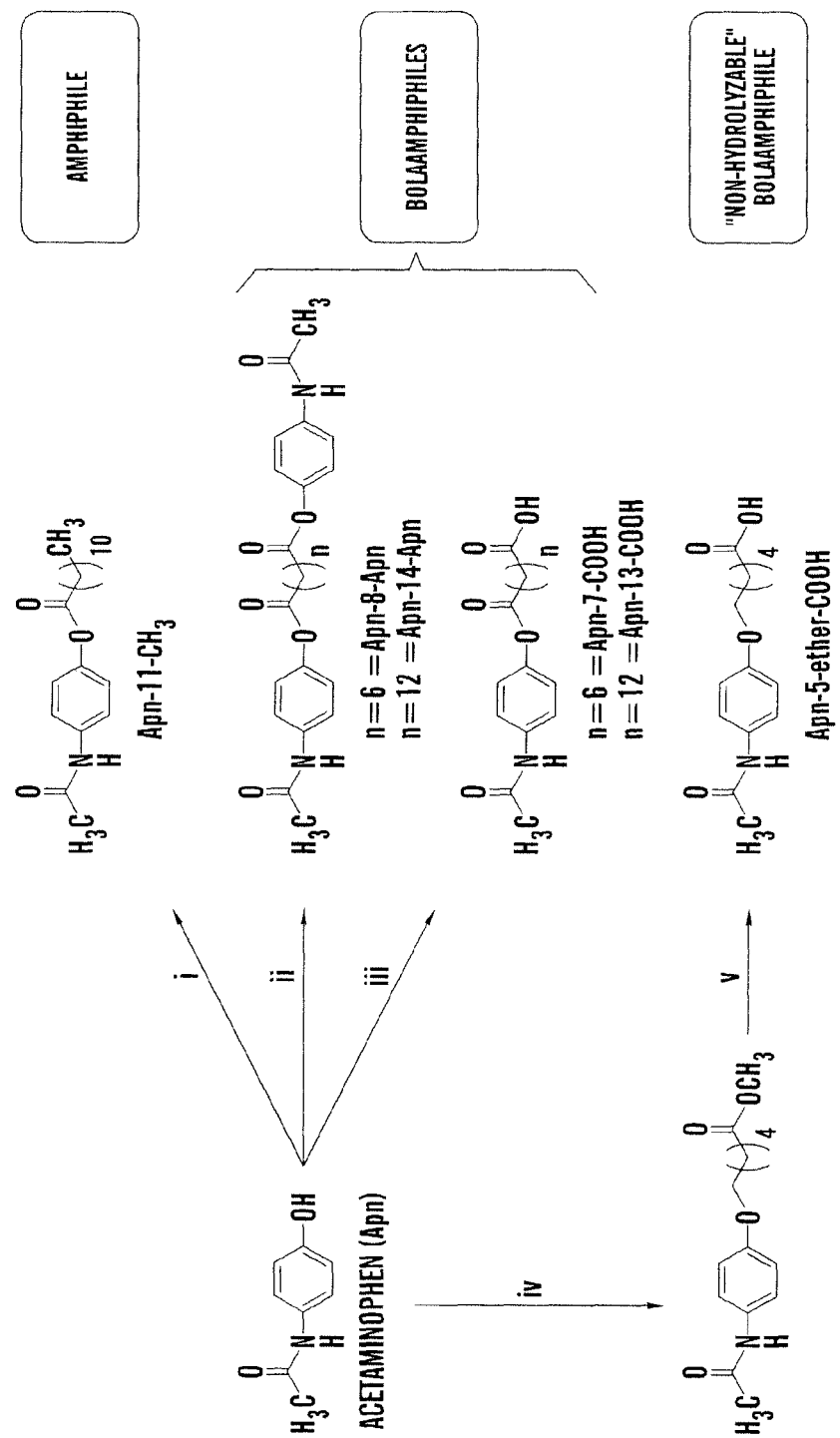
FIG. 2 is a schematic representation of synthesis of amphiphiles and bolaamphiphiles from acetaminophen.
Figure 3E:
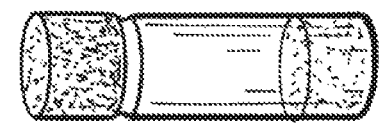
FIG. 3E shows the real image of the hydrogel of FIG. 3A.
Figure 3B:
FIGS. 3A, 3B, 3C, and 3D depict SEM images of hydrogels made from Apn-7-COOH (3A), and Apn-8-Apn (3B). Unstained TEM images of hydrogels made from Apn-7-COOH (3C), and Apn-8-Apn (3D).
Figure 3D:
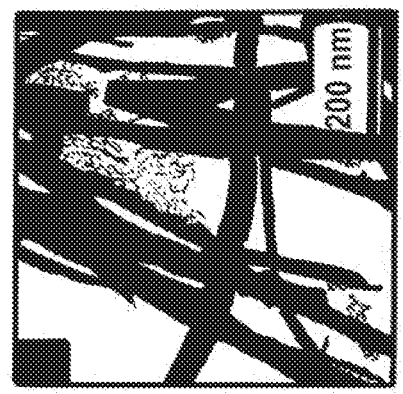
Figure 3A:
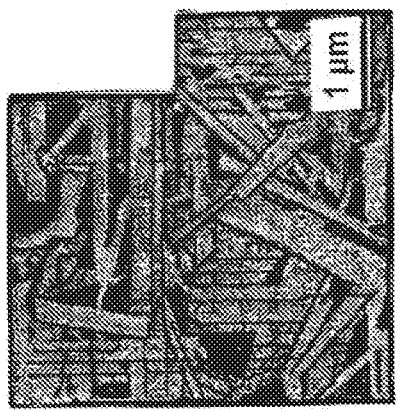
Figure 3C:
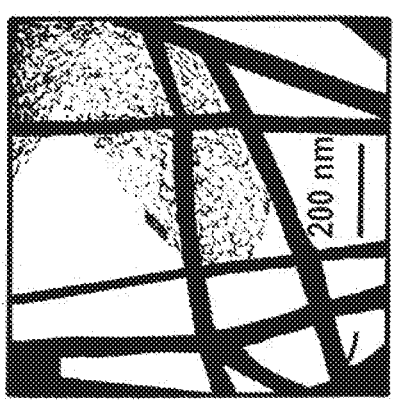
Figure 5E:
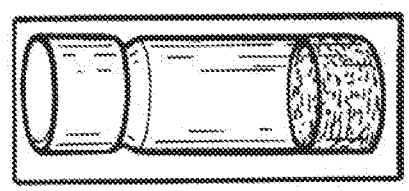
FIG. 5E shows the real image of the hydrogel of FIG. 5A.
Figure 5B:
FIGS. 5A, 5B, 5C and 5D depict SEM images of curcumin encapsulated hydrogels made from Apn-7-COOH (5A), and Apn-8-Apn (5B). Unstained TEM images of curcumin encapsulated hydrogels made from Apn-7-COOH (5C), and Apn-8-Apn (5D).
Figure 5D:
Figure 5A:
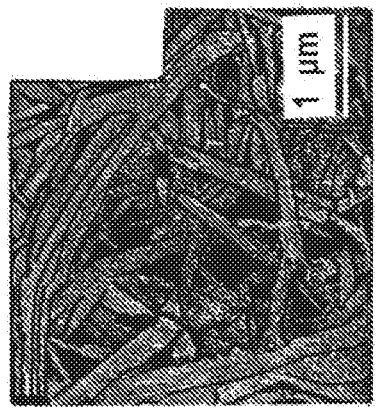
Figure 5C:
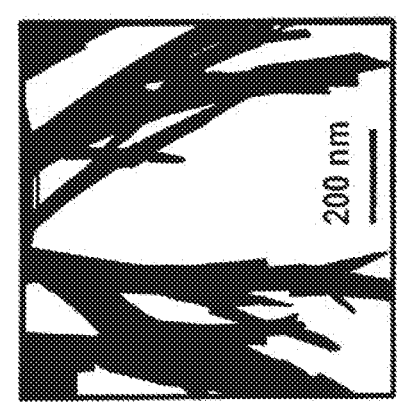

A series of amphiphiles and bolaamphiphiles were synthesized in a single step from Apn as shown in FIG. 2. The designed Apn based prodrugs encompass functional groups which can promote intermolecular molecular interactions through hydrogen bonding, pi-pi stacking and van der Waals interactions.

Design and Synthesis of Prodrug-Based Gelators. Design of amphiphilic gelators from known drugs is a challenging task. During this process the following parameters were used: i) the drug molecule had a functional group which can be easily functionalized under mild conditions; ii) the functionalized drug (prodrug) was able to undergo defunctionalization (reversible) under 'triggered' conditions to release the parent drug; iii) the drug has the ability to promote self-assembly, or introducing appropriate additional groups. While small molecular drugs have previously been combined with polymers (see Huang, X.; Brazel, C. S. *J. Controlled Release* 2001, 73, 121-136) or polymeric micelles (see Hans, M.; Shimoni, K.; Danino, D.; Siegel, S. J.; Lowman, A. *Biomacromolecules* 2005, 6, 2708-2717; and Kim, S. C.; Kim, D. W.; Shim, Y. H.; Bang, J. S.; Oh, H. S.; Wan-Kim, S.; Seo, M. H. *J. Controlled Release* 2001, 72, 191-202), it is believed that there are no reports on developing single and multiple drug delivery vehicles from self-assembled prodrugs. Hence, Apn was chosen for generating prodrug based hydrogelators.

Apn encompass acetamide group which can promote hydrogen bonding while phenyl ring can facilitate intermolecular associations through pi-pi stacking. However it is also water soluble. Thus, the addition of a biocompatible fatty acid through a labile ester linker (Apn-11-$CH_3$) will insert the ability to form van der Waals interactions into amphiphile. To improve the polarity for dispersion into water upon heating, bolaamphiphiles were designed. See Scheme 2. Introducing a terminal carboxyl group (Apn-7-COOH and Apn-13-COOH) renders multiple advantages such as increasing the polarity, additional hydrogen bond forming ability through carboxylic groups and the possibility to better control the self-assembly through pH variation. Symmetrical bolaamphiphiles were synthesized connecting two Apn molecules through a dicarboxylic acid linker (Apn-8-Apn and Apn-14-Apn). In addition, to probe the mechanistic properties of enzyme triggered gel degradation and drug delivery, a hydrocarbon chain was coupled through a non-hydrolyzable ether linker (Apn-5-ether-COOH, Scheme 2), which also has a terminal carboxylic group. Hence it can retain its self-assembling ability. Apn based amphiphiles and bolaamphiphiles were synthesized using synthetic techniques in a single step, as shown in FIG. 2 and the Experimental section, below. It is believed that this synthetic route can be used to develop these gelators in industrial scales for various applications.

Gelation Studies with Prodrug-Based Gelators. Gelation abilities of Apn based amphiphilic prodrugs have been investigated thoroughly in a wide range of solvents. For detailed gelation results, see Table 1, below). Typically, the required amount of gelator was placed in a glass vial and with an appropriate solvent. Subsequent heating resulted in the dissolution of the gelator. The resulting solution was slowly cooled to room temperature and gelation was visually observed. Gelation was confirmed when no gravitational flow was observed in an inverted vial. All Apn based amphiphiles were observed to be good thermoreversible gelators. Amphiphile Apn-11-$CH_3$ did not gelate in water while gelating various organic solvents. Despite of prolonged heating Apn-11-$CH_3$ was not soluble in water. In contrast, Apn-7-COOH forms excellent gels in water and other aqueous buffer solutions even in presence of salt. In addition, Apn-7-COOH is soluble in basic solutions (pH is more than 8). This shows that terminal carboxylic acid groups play a role in self-assembly, possibly through formation of hydrogen bonding network. However, due to longer hydrophobic chain Apn-13-COOH was sparingly soluble in water and thus additional co-solvent (5-15 v/v % of alcohol such as methanol, ethanol or isopropanol) was used to make the hydrogel. Symmetrical bolaamphiphile Apn-8-Apn formed stable hydrogels while Apn-14-Apn was insoluble in water.

These results show that a balance of solvophobic and solvophilic is desirable while other functional groups promote intermolecular interactions such as hydrogen bonding, pi-pi stacking and van der Waals interactions. All gelators showed lower minimum gelation concentrations (between 0.4-1.5 w/v % and millimolar concentrations, Table S1). Gel to solution transition temperature ($T_{gel}$) was determined by typical inversion-tube-method (see, for example Vemula, P. K.; John, G. *Chem. Commun.* 2006, 2218-2220, and F. M.; Caran, K. L. *J. Am. Chem. Soc.* 2000, 122, 11679-11691) and they exhibited values between 60-82° C. for 1 wt % of gels depending on the solvent used. All gels were opaque in nature and stable for several weeks. These results indicate that prodrug based hydrogels exhibit high thermal and temporal stabilities. Detailed gelation results are shown in Table 1.

Hydrogel Morphology. The morphologies of self-assembled hydrogels were examined under scanning and transmission electron microscopy (SEM and TEM, respectively). Investigation of the hydrogels of Apn-7-COOH and Apn-8-Apn with SEM and TEM showed that prodrug gels form branched or entangled fibrous/sheet-like gel networks with fiber thickness of 50-400 nm, and fiber lengths of several microns (FIGS. 3A-3E). The high aspect ratios of the gel fibers indicate that the intermolecular interactions between the gelator molecules are highly anisotropic. In addition, lower gelation concentrations and high temporal stability of the gels suggest that the intermolecular interactions are more prevalent and thus most likely the result of the synergistic effect of both pi-pi interactions and hydrogen bonding.

Figure 15:
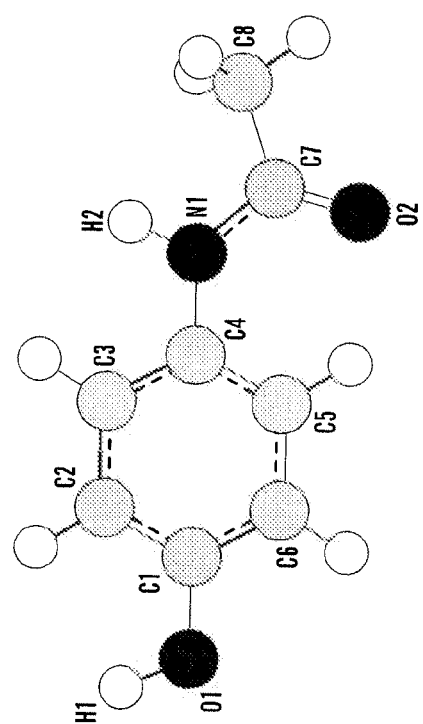
FIG. 15 is a schematic representation of Apn showing atom numbering used to report selected geometric parameters.

Self-Assembly in Hydrogels. Optimized geometries were obtained and the lengths of gelators were calculated using ab initio calculations. By combining the data from X-ray diffraction (XRD) and Fourier transform infrared spectroscopy (FT-IR) a model for self-assembly of amphiphilic prodrugs in aqueous solution was proposed. All the ab initio Hartree-Fock calculations reported were performed using the Gaussian 03 suite program (Frisch, M. J. et al. *Gaussian* 03, Revision B.03; Gaussian, In.: Pittsburg, Pa., 2003). The geometries of Apn-7-COOH and Apn-8-Apn have been located and optimized at the level of restricted Hartree-Fock (RHF) using the 6-31G* basis set (Hehre, W. J.; Radom, L.; Schleyer, P. V. R. *Ab Initio Molecular Orbital Theory*; Wiley & Sons: New York 1986, pages 63-91. All structures were completely optimized without any symmetry restrictions. For both molecules studied, vibrational frequency calculations were carried out to confirm that they converge to true minima by diagonalization of their Hessian (force constant) matrixes at the same level and making sure that all frequencies are real. To check the reliability of the level of theory, Apn was optimized using RHF/6-31G*, thus geometrical parameters were compared with the reported crystal structure of Apn (FIG. 15, Table 2). Fully optimized geometries of both amphiphilic prodrugs are shown in FIG. 4A, and calculated lengths are 1.97 and 2.67 nm for Apn-7-COOH and Apn-8-Apn, respectively.

The hydrogels obtained from prodrugs Apn-7-COOH and Apn-8-Apn displayed well-resolved X-ray diffraction (XRD) patterns that were characteristic of the long-range ordering of the gelators. The long spacing (d) was calculated to postulate the possible mode of self-assembly in the gel state. Long distance spacing values suggest that possibly lamellar structures were formed by these gelators in the gels. In XRD measurements, the hydrogel of Apn-7-COOH ad of 3.53 nm, which is higher than the molecular length of Apn-7-COOH (1.97 nm from the optimized geometry calculations, FIG. 4A) and slightly lower than double the molecular length. Therefore, it can be predicted that amphiphiles are tilting with respect to normal to the layer plane (FIG. 4B).

The hydrogel of Apn-8-Apn showed two major d values of 2.72 and 4.9 nm. In the case of d=2.72 which is close to the molecular length of Apn-8-Apn, it is believed that a monolayer-like structure exists which could be stabilized by strong intermolecular interactions such as hydrogen-bonding, pi-pi interactions, as shown FIG. 4C. Additionally, acetaminophen groups of two adjacent layers could form strong hydrogen-bonding as shown in FIG. 4D which supports the observed d value 4.9 nm. In addition, FT-IR experiments were performed to gain insight into the hydrogen-bonding environment of the amide carbonyl (C=O) group in Apn-8-Apn under solution and gel conditions. In the methanolic solution of Apn-8-Apn, an amide I band appeared at 1663 $cm^{-1}$ whereas in gel state it shifted to 1631 $cm^{-1}$. Such a significant shift of 32 $cm^{-1}$ could be attributed to the strong hydrogen-bonding interactions of the carbonyl groups of acetamides in the gel state which suggests that hydrogen-bonding enhances the self-assembly of these amphiphilic prodrugs to form hydrogels. Thus, based on the information obtained from the theoretical calculations, FT-IR and XRD experimental results, a model for the self-assembly of these amphiphiles has been proposed, as shown in FIGS. 4A-4D.

Enzyme-Mediated Single and Multiple Drug Release. Many potent therapeutic agents possess a high degree of hydrophobicity which can impede their solubilization in aqueous media and thus hamper their oral or parenteral administration. In order to circumvent this limitation, suitable biocompatible drug delivery systems can be developed which can provide increased surface area for it to dissolve by providing many hydrophobic drug molecules throughout the assembled gel. In this example, the encapsulation of hydrophobic drug in a prodrug-based hydrogel is demonstrated, which upon enzyme-mediated gel degradation releases single and multiple drugs at physiological conditions in a controlled manner.

To investigate single and multiple drug delivery from Apn-based prodrug hydrogels, the well-known chemopreventive drug curcumin was chosen as a model hydrophobic drug for encapsulating into hydrogels. Curcumin (1,7-bis(4-hydroxy-3methoxyphenyl)-1,6-heptadiene-3,5-dione) was originally extracted from the root of *Curcuma longa*, and it is the main constituent of the Indian spice turmeric, and give curry sauces their characteristic yellow color. This molecule shows a wide range of pharmaceutical activity, including potent antioxidant, anti-inflammatory, antiseptic and anti-carcinogenic properties. It also exhibits promising therapeutic activity by inhibiting various purified human immunodeficiency virus (HIV) types.

However, in spite of promising drug activity, curcumin has an extremely poor bioavailability due to particularly its low solubility in aqueous solutions (solubility of curcumin in water is $3 \times 10^{-8}$ M). Previously, Tang et al. demonstrated increased solubility of curcumin in water by forming supramolecular host-guest complex with various cyclodextrins (Tang, B.; Ma, L.; Wang, H.-Y.; Zhang, G.-Y. *J. Agric. Food Chem.* 2002, 50, 1355-1365). Hence, it would be possible to increase curcumin concentration in water by encapsulating into hydrogels where abundant hydrophobic regions are available. Hydrogels of Apn-7-COOH or Apn-8-Apn could encapsulate high concentrations of curcumin (up to 0.5 mmol); the observed enhanced concentration is believed to be due to localization of hydrophobic curcumin within the hydrophobic pockets of hydrogels three-dimensional network.

To examine the effect of external drug encapsulation on the inherent morphology of the self-assembled gel, curcumin-encapsulated hydrogels were examined under SEM and TEM (FIGS. 5A-5E). Encapsulation of curcumin did not affect the morphology of the hydrogels. It is believed that self-assembly phenomenon could be identical or nearly identical in both types of hydrogels (with and without curcumin), as there was no significant difference in the morphology of the native hydrogels and curcumin encapsulated hydrogels (see FIGS. 3A-3E and FIGS. 5A-5E, respectively).

Encapsulation and release of curcumin was previously studied by the Ultra-Violet absorbance spectroscopy ($\lambda$max at 424 nm). Absorbance spectrum of modified Apn-7-COOH was similar to that of Apn (FIG. 6B). In this instance, enzyme-triggered single and multiple drug delivery has been carried out using two sets of hydrogel samples, i.e., hydrogels of Apn-7-COOH and Apn-8-Apn with and without curcumin. In the first set, lipase (Lipolase 100L, Type EX, lipase units 100 KLU/g) was added to the preformed hydrogel of Apn-7-COOH (2 wt %) and kept it at 37° C. which is lower than gel melting temperature. It was anticipated that lipase (esterase) would hydrolyze the ester bond of prodrug-based gelator (Apn-7-COOH) to release acetaminophen and dicarboxylic acid as the hydrogel degrades. As expected, after 48 hours the gel completely degraded and became a clear solution. UV-absorption experiments could not study the release of original drug acetaminophen (Apn), as absorbance peaks of Apn and lipase overlap significantly. Hence, thin-layer chromatography was performed on resulted clear solution, which indicated that indeed acetaminophen and $\alpha,\omega$-dicarboxylicacid were generated in the solution. This suggests that the gel degradation is occurring through the cleavage of ester bonds within the acetaminophen-based prodrugs by lipolase enzyme.

Figure 6A:
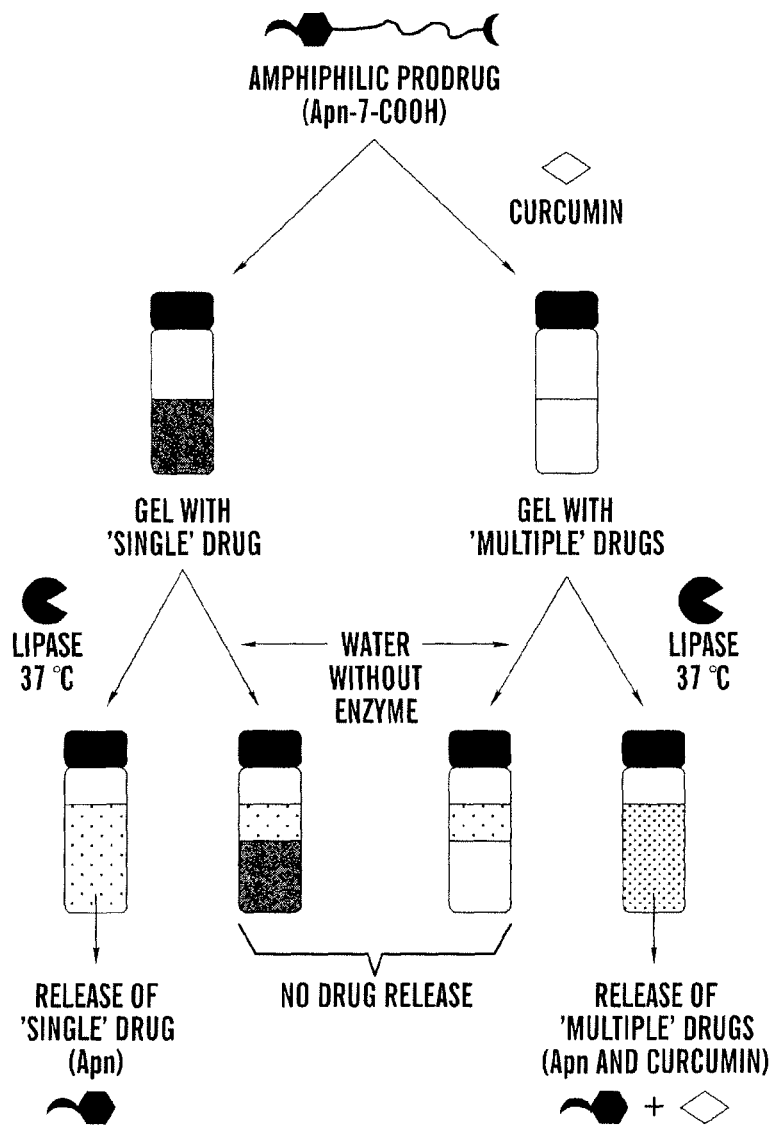
FIG. 6A shows a schematic representation of enzyme-mediated single and two drugs delivery from Apn-based prodrug hydrogels.

To test this further, and examine multiple (two) drugs delivery (FIGS. 6A-6E), curcumin was encapsulated in the hydrogel of Apn-7-COOH (2 wt %) and to that lipase was added and kept it at 37° C. Absorbance spectra were recorded on aliquots which were collected (after the addition of enzyme to the hydrogel) at regular intervals (FIG. 6C). Plotting absorbance maxima vs time (FIG. 6E) reveals absence of burst release which is otherwise a routine hurdle in hydrogel-based drug release. Initial aliquots did not show any absorbance peak, but aliquots collected after 4 hrs showed absorption maxima at 425 nm, which corresponds to the absorption peak of curcumin. The concentration of the enzyme used in these in vitro experiments is higher than physiological concentration of esterases (for example, physiological concentration of cholesterol esterase is 7 U/ml). Hence it was anticipated that under in vivo conditions the present system would show prolonged sustained release.

To determine the role of the enzyme on hydrogel degradation, similar experiments were performed by adding only buffered solution without an enzyme. As expected, curcumin encapsulated gel was still intact over a month, there was no visual change in the gel volume and added solution, and no absorbance peaks corresponding to the curcumin were observed, suggesting that the enzyme is effective in the gel degradation. In addition, it also suggests that the curcumin release which was observed in the previous experiment is due to degradation of hydrogel. There was no loosely absorbed curcumin on hydrogels to diffuse into the water with time. Hence, it is believed that the encapsulated curcumin intercalates within in the hydrophobic pockets of self-assembled fibers.

The yellow color cleared solution which was obtained after enzyme mediated gel degration was also tested by thin-layer chromatography, and found that Apn and curcumin are present; thus, it confines the synergistic release of Apn and curcumin which indicate that this approach could be used to develop delivery vehicles to release two drugs (possible complimentary drugs) simultaneously or nearly simultaneously. Increasing either concentration of enzyme or incubation temperature to 45° C. doubles the drug release rate, which was correlating with previous findings.

To analyze the gel degradation mechanism, another prodrug Apn-5-ether-COOH was synthesized (FIG. 2), where hydrocarbon chain (which is bearing terminal carboxylic acid) was connected to the acetaminophen through an ether bond (C—O—C) to prevent the esterolytic cleavage by lipase. Apn-5-ether-COOH exhibited gelation behavior akin to Apn-7-COOH; curcumin has been encapsulated into Apn-5-ether-COOH hydrogel, and to that lipase was added. After incubating at 37° C. for several days, the hydrogel was still intact and prevented curcumin release into the solution (confirmed by absorption spectroscopy) which suggests that the lipase cleaves the prodrug gelator at the ester bond to release Apn and encapsulated curcumin. Hence, having a cleavage labile ester group is desirable when preparing the prodrug based hydrogelators.

Cytocompatibility. The cytocompatibility of prodrugs generated from small modification of known drugs was investigated. This was done to demonstrate that chemical modification on Apn did not introduce cytotoxicity into the molecule. To test the cyto compatibility of prodrug-based amphiphiles and bolaamphiphiles, and their effect on cell characteristics such as viability, proliferation, adhesion and cell phenotype, a series of experiments was performed with mesenchymal stem cells (MSCs). To gain more insight into the effect of modification, unmodified drug Apn was used as a control. The viability of control cells and cells treated with Apn, Apn-7-COOH and Apn-8-Apn was examined with trypan blue assay. Use of Mesenchymal stem cells is appropriate given that these systems may be used for localized release likely into connective tissues.

Figure 7A:
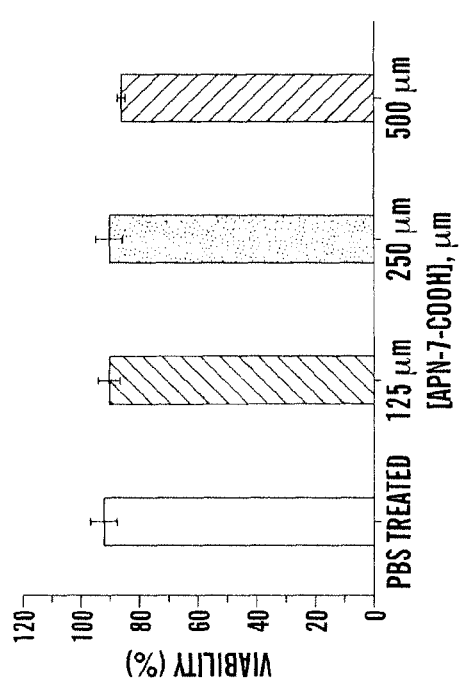
FIGS. 7A, 7B, 7C and 7D depict graphs showing the effect of Apn-based prodrugs on MSCs cellular properties such as viability (7A) and (7B), adhesion (7C) and proliferation (7D). Cell viability was examined after 48 hours (7A and 7B), adhesion was measured after 12 hours (7C). Concentration of Apn and other amphiphiles used in a, c and d are 250 µM.

The results (FIG. 7A) suggest that there was no significant decrease in the viability of the MSCs after 48 hours incubation with prodrug-based amphiphiles. Specifically, 95% of untreated cells were viable after 48 hours, whereas 91%, 87% and 82% of viable cells were observed for cells incubated with 250 µM of Apn, Apn-7-COOH and Apn-8-Apn, respectively (FIG. 7A).

Figure 7B:
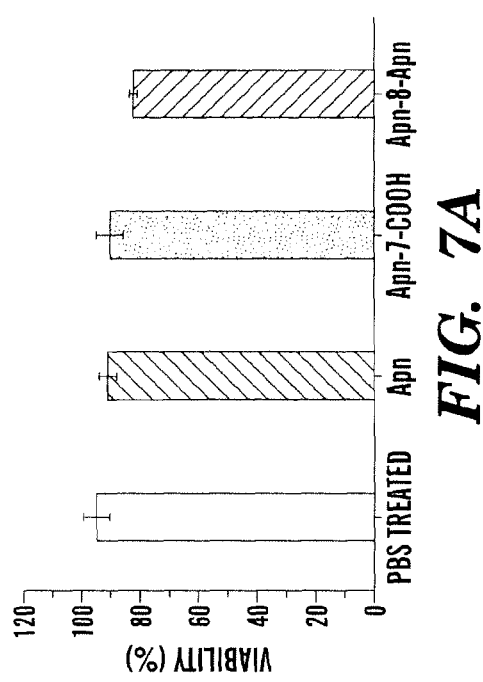
Figure 7C:
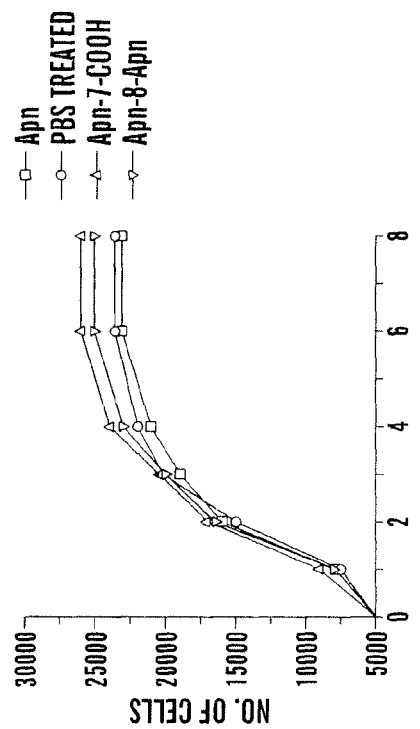

In another set of experiments, it was determined that viability rates were not significantly affected by a wide range of concentration of Apn-7-COOH (up to 500 µM, FIG. 7B). These results show that Apn-derived prodrug amphiphiles did not induce cell toxicity. To test how prodrug hydrogelators will affect the extracellular environment of MSCs, cell adhesion characteristics were examined (after 12 hrs), and it was found that in presence of Apn-based amphiphiles there was no considerable change in adhesion properties of MSCs (FIG. 7C).

Figure 7D:
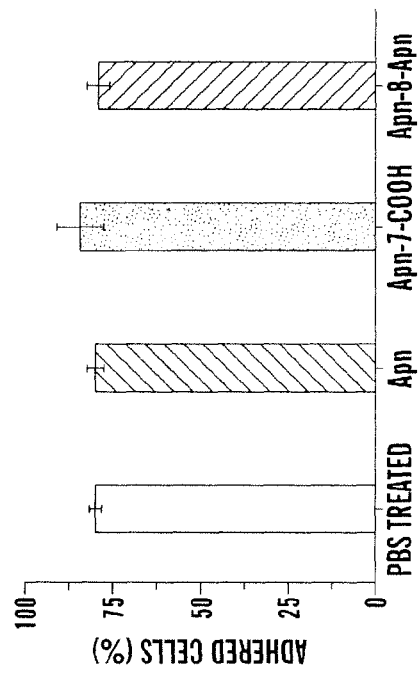
Figure 8E:
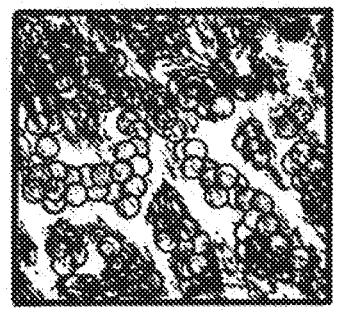
FIG. 8E shows the magnified region on fat droplets of FIG. 8A.
Figure 8B:
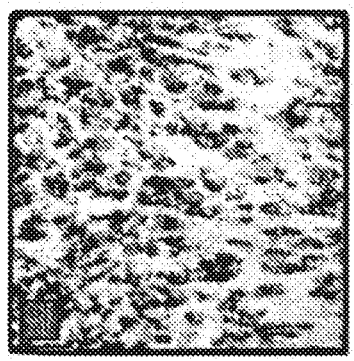
FIGS. 8A, 8B, 8C, and 8D depict results of adipogenesis after 23 days of induction as observed by Oil Red O (ORO) staining. Controls cells treated with phosphate buffer saline (PBS) (8A), and 250 µM Apn (8B) showed positive staining. Cells treated with 250 µM of Apn-7-COOH (8C) and Apn-8-Apn (8D) were also equally stained for ORO. In all images scale bar=100 µm.
Figure 8D:
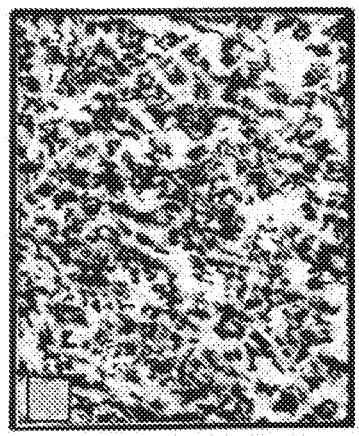
Figure 8A:
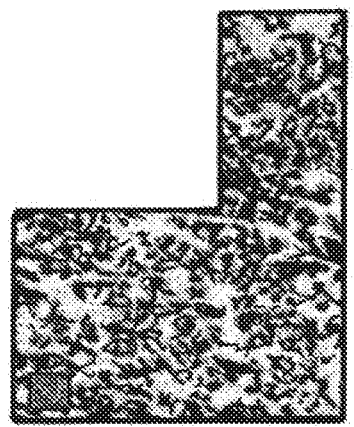
Figure 8C:
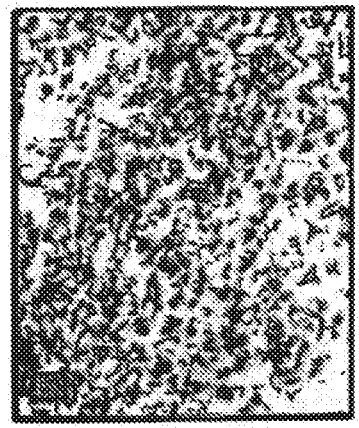
Figure 9E:
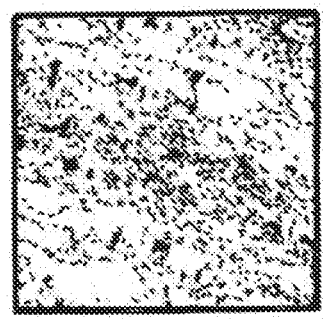
FIG. 9E shows the magnified region of differentiated cells, and black spots are mineralized foci localized to ALP stained cells of FIG. 9A. In all images scale bar=100 µm.
Figure 9B:
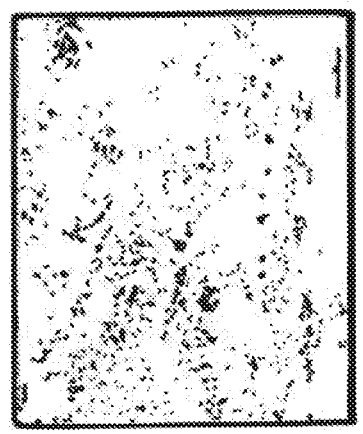
FIGS. 9A, 9B, 9C and 9D depict results of osteogeneis after 23 days as observed by alkaline phosphatase (ALP) staining. Controls cells treated with phosphate buffer saline (PBS) (9A), and 250 µM Apn (9B) were showed positive staining. Cells treated with 250 µM of Apn-7-COOH (9C) and Apn-8-Apn (9D) were also equally stained for ALP.
Figure 9D:
Figure 9A:
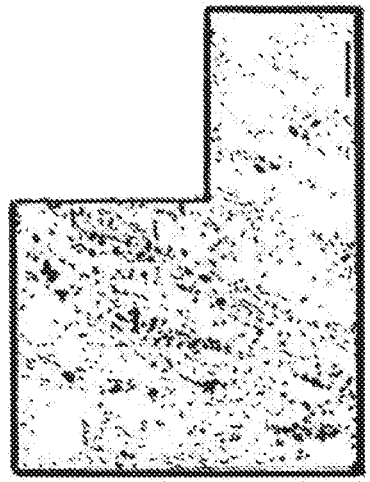
Figure 9C:

The proliferation rate of MSCs was also examined. In all cases (cells treated with buffer and cells treated with Apn, Apn-7-COOH and Apn-8-Apn) cells proliferated to attain a confluent layer, and were found to have similar proliferation rates (FIG. 7D). This indicates that the presence of prodrug-amphiphiles did not alter the proliferation of MSCs.

Ethanol was used to dissolve amphiphiles, with the total volume of the ethanol being 1 v/v % in the experiments. To exclude the possibility that observed small changes in viability, adhesion and proliferation results was caused by ethanol, in every experiment, the control was used where cells were treated with 1 v/v % of ethanol. The results (not shown here) demonstrate that ethanol did not significantly affect the viability, adhesion and proliferation.

Unlike typical fibroblast cell lines used for toxicity screening, cultured mesenchymal stem cells are highly sensitive to the presence of soluble factors and can often loose their capacity for multi-lineage differentiation or differentiate into non-desired lineages depending on the culture conditions. To examine the impact of the acetaminophen amphiphilic prodrugs on multi-lineage differentiation of MSCs, cells were treated with adipogenic and osteogenic induction media in presence of amphiphiles followed by respective colorimetric histological staining. Even in presence of Apn, Apn-7-COOH and Apn-8-Apn, the MSCs showed a robust capacity differentiated into adipogenic (FIGS. 8A-8E) and osteogenic (FIGS. 9A-9E) lineages as shown by oil red O (ORO) staining and alkaline phosphatase (ALP) activity, respectively. No significant difference in ORO or ALP staining was observed for MSCs treated with and without Apn-based prodrug amphiphiles. Thus, the modified prodrugs did not impair the potential for multi-lineage differentiation. Hence, the Apn-based prodrugs are cytocompatible and do not amend the inherent cellular properties of MSCs.

Figure 10A:
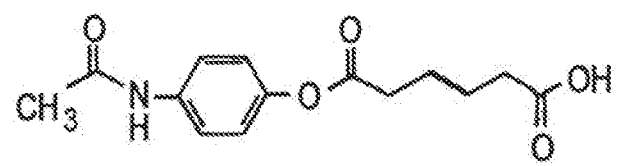
FIG. 10A is the chemical structure of an acetaminophen-based prodrug that is synthesized by modifying acetaminophen with a biocompatible fatty acid.
Figure 10B:
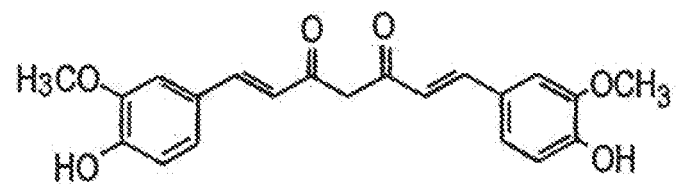
FIG. 10B is the chemical structure of curcumin.
Figure 10C:
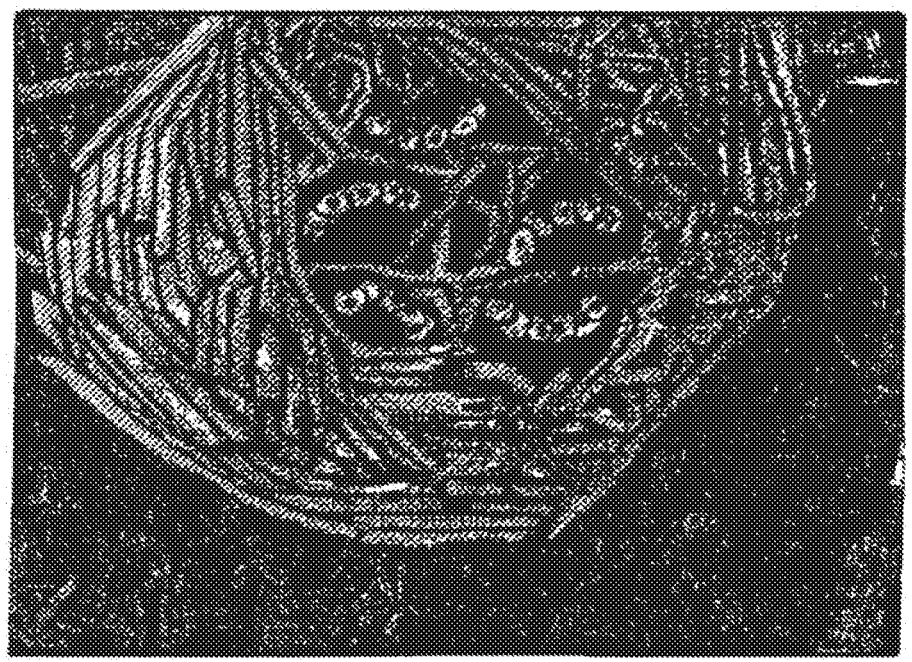
FIG. 10C illustrates the self-assembled acetaminophen-derived gelators depicted in FIG. 10A encapsulating the drug depicted in FIG. 10B.

Example 1 demonstrates that amphiphilic low-molecular-weight prodrug hydrogelators have been synthesized from simple modification of known-drug acetaminophen by combining a biocompatible fatty acid. The acetaminophen-based prodrugs self-assembled to form hydrogels. A known chemopreventive hydrophobic drug curcumin has been encapsulated into the hydrogels, subsequently; enzyme-triggered single and multiple drug (one and two drugs) delivery had been demonstrated at physiological conditions in vitro. See FIGS. 10A-10C.

These prodrugs exhibited excellent self-assembling properties to form hydrogels at low concentrations. Mode of self-assembly in hydrogels was proposed based on the XRD, FTIR data and theoretical calculations. The encapsulation of chemopreventive curcumin in the hydrogels which were prepared from Apn-based prodrugs was shown, and enzyme-triggered gel degradation was performed to achieve single and multiple drug delivery in vitro at physiological conditions. In addition, it was found that the modified Apn-based prodrugs are excellent cytocompatible amphiphiles, and do not alter mesenchymal stem cell properties such as viability, adhesion, proliferation and ability to differentiate into multiple lineages including adipogenic and osteogenic. These results suggest that self-assembled hydrogelators from existing drugs which have known metabolic pathway can be used in the field of low-molecular-weight hydrogelators based drug delivery.

Experimental Section

General Information. Acetaminophen and curcumin were purchased from Acros Chemicals (Fisher Scientific Company, Suwane, Ga.). The Novozyme 435 [lipase B from *Candida antarctica*, (CALB)] and Lipolase 100L was obtained from Novozymes through Brenntag North America. Human MSCs were obtained from the Center for Gene Therapy at Tulane University. α-MEM, Fetal Bovine Serum, L-Glutamine and Penn-Strep were purchased from Invitrogen. All other chemicals and reagents were purchased from Sigma Aldrich (St. Louis, Mo.) and were used without further purification unless specified.

Synthesis of Hydrogelators. For detailed synthesis procedures and characterization of compounds see Supporting Information, below.

Preparation of Gels. Typically, gelator (0.1-5 mg) and required solvent (0.1-1 mL) were placed into a 2 mL scintillation vial, which was then sealed with a screw cap. The vial was heated with shaking until the solid was completely dissolved. Gelation was considered to be occurred when no gravitational flow was observed in the inverted tube, when vial reached to the room temperature.

Gel Melting Temperatures. Gel to Sol transition temperature ($T_{gel}$) was determined typical 'inversion tube method' (see, P. K.; John, G. *Chem. Commun.* 2006, 2218-2220, and Menger, F. M.; Caran, K. L. *J. Am. Chem. Soc.* 2000, 122, 11679-11691) where gel was prepared in a 2 mL glass vial by dissolving 1 wt % gelator in required amount of solvent and closed with tight screw cap. The vial was immersed in the water 'up side down' and slowly heated, where the viscous gel has melted dropped down that temperature was considered as $T_{gel}$.

Scanning Electron Microscopy. To record SEM, the xerogel samples were prepared by freezing-and-pumping method from their gel phases below the sol-gel transition temperature. The SEM images of xero gels and the following drying under ambient condition show similar morphologies. Therefore, morphology with the gels was studied dried under ambient conditions, (called xerogels).

Transmission Electron Microscopy. TEM was recorded by using Zeiss EM 902 transmission electron microscope (80 kV). A small portion of gel was drop cast on a Cu-grid. After drying the grid at ambient temperature, it was directly imaged under TEM.

UV-vis Spectroscopy. UV-visible spectra of the amphiphiles and curcumin were were recorded using CARY100BIO spectrophotometer. In all experiments, solutions were taken in quartz cuvette of 1-cm path length.

X-ray Diffraction (XRD). XRD measurements were conducted using a Bruker AXS D-8 Discover with GADDS diffractometer using graded d-space elliptical side-by-side multilayer optics, monochromated Cu-Kα radiation (40 kV, 40 mA), and imaging plate.

Mesenchymal Stem Cell Culture. Primary human mesenchymal stem cells were maintained in expansion media that consisted of 15% Fetal Bovine Serum (selected for its ability to expand MSCs), 1% (v/v) L-Glutamine, 1% (v/v) Penn-Strep, and α-MEM. All experiments were performed using MSCs at passage number 4-6.

Viability, Adhesion and Proliferation Characteristics. The viability of the cells was examined using trypan blue exclusion. Cells were plated into 12 well plates, to that 250 µM of Apn or Apn-based prodrugs were added, and incubated for 48 hours at 37° C. and 5% $CO_2$. The media was then aspirated and the cells were detached with 200 µL of cell dissociated solution (similar quantities of floating cells were observed between the groups, typically 5-10 per well). 300 µL of media was added and the total 500 µL of the cell dispersion was collected in an eppendorf tubes. From this 10 µL of cell dispersion was diluted to 1:1 with 4% trypan blue solution and cells were counted in a hemocytometer to determine the number viable (non-blue) and nonviable (blue) cells. A control for this experiment included cells treated with only phosphate buffer saline (PBS) without an amphiphile. Cell adhesion was quantified by measuring the number of adherent cells on tissue culture surfaces in 96 well plates after incubating with amphiphiles for 12 hours. For proliferation studies, 5000 cells were added to each well of a 96 well plate in 200 µL of MSC cell expansion media, and appropriate amphiphiles were then added and incubated at 37° C. and 5% $CO_2$. Proliferation was quantified by manually tabulating the number of cells within the flask at multiple time points (1, 2, 3, 4, 6 and 8 days) with light microscopy at 10×.

Osteogenic Differentiation. MSCs were seeded in the wells of 24 well plates, and were culture in MSC expansion media until they reach 90% confluence (note: in control samples there was no amphiphile present, whereas in experimental samples 250 µM of Apn-based amphiphile was present). Osteogenic differentiation was induced by culturing the cells for 23 days in osteogenic induction media (from Lonza—MSCs Osteogenic Single Quote kit) containing dexamethasone, β-glycerophosphate, L-ascorbic acid-2-phosphate, and α-MEM. The media in both groups was changed every 3 days (note: each time while changing the media, 250 µM of Apn-based amphiphiles were added to maintain constant concentration). Osteogenesis was evaluated by cell membrane associated alkaline phosphatase activity. Alkaline phosphatase activity was examined after 23 days by carefully aspirating the media and washing the cells with PBS. The cells were fixed with 3.7% formaldehyde solution for 15 min at room temperature followed by rinsing with distilled water. 0.06% Red Violet LB salt solution in Tris HCl was added with distilled water containing DMF and Naphthol AS MX-$PO_4$. The plates were incubated for 45 minutes at room temperature and then the wells were rinsed 3 times with distilled water and imaged under with inverted phase contrast microscope.

Adipogenic Differentiation. MSCs were seeded in the wells of 24 well plates, and were culture in MSC expansion media until they reach 90% confluence (note: in control samples there was no amphiphile present, whereas in experimental samples 250 µM of Apn-based amphiphile was present). Adipogenic differentiation was induced by culturing the cells for 23 days in adipogenic induction media (from Lonza—MSCs Adipogenic Single Quote kit containing h-Insulin (recombinant), L-Glutamine, Dexamethasone, Indomethacin, IBMX (3-isobuty-1-methyl-xanthine), Pen/Strep) and adipogenic maintenance media (from Lonza—MSCs Adipogenic Single Quote kit containing h-Insulin (recombinant), L-Glutamine, Pen/Strep). The media in both groups were changed every 3 days in a periodic exposure of induction and maintenance media as suggested by the supplier (Lonza), (note: each time while changing the media, another 250 µM of Apn-based amphiphiles were added to maintain constant concentration). Adipogenesis was evaluated by Oil Red O staining. Following aspiration of the media, cells were washed once with PBS, and fixed in PBS with 3.7% formaldehyde for 30 min at room temperature. Following fixation cells were rinsed with distilled water for a few minutes, and incubated with isopropanol containing an Oil Red O working solution (prepared by diluting 30 mL of 0.5% isopropanol/Oil Red O solution with 20 mL of distilled water). After 45 minutes culture well were rinsed twice with distilled water and 1 mL of hematoxylin was added to each well for 1 minute followed by aspiration and washing with distilled water. The wells were viewed using an inverted phase contrast microscope.

TABLE 1

Gelation ability of acetaminophen-based prodrug hydrogelators.[a]

| solvent | Apn-11-$CH_3$ | Apn-7-COOH | Apn-13-COOH | Apn-8-Apn | Apn-14-Apn |
|---|---|---|---|---|---|
| water | I | G (0.4) | G (0.6) | G (1.1) | G (0.9) |
| methanol | S | S | S | S | S |
| ethanol | G (1.5) | S | S | S | S |
| isopropanol | G (0.8) | I | S | S | S |
| t-butanol | G (0.6) | I | S | S | S |
| ethyl acetate | P | I | I | I | I |
| chloroform | S | S | S | S | S |

[a]Values in the parenthesis are minimum gelation concentration (wt/v %). G = gel, P = precipitate, S = soluble, I = insoluble.

TABLE 2

Selected geometric parameters (bond lengths, Å) of Apn obtained from ab initio calculation and compared with reported crystal structure. Inset optimized geometry of Apn using restricted Hartree Fock level theory and 6-31G* basis set. Atom numbering of Apn is shown in FIG. 15.

| | crystal structure[a] | RHF/6-31G* |
|---|---|---|
| O1—C1 | 1.375 | 1.355 |
| C1—C2 | 1.396 | 1.382 |
| C2—C3 | 1.385 | 1.385 |
| C3—C4 | 1.396 | 1.386 |
| C4—C5 | 1.396 | 1.393 |
| C5—C6 | 1.388 | 1.381 |
| C6—C1 | 1.389 | 1.385 |
| C4—N1 | 1.426 | 1.413 |
| N1—C7 | 1.346 | 1.361 |
| C7—O2 | 1.239 | 1.197 |
| C7—C8 | 1.509 | 1.516 |
| O1—H1 | 0.92 | 0.94 |
| N1—H2 | 0.92 | 0.99 |

[a]Naumov, D. Y.; Vasilchenko, M. A.; Howard, J. A. K. Acta Cryst. 1998, C54, 653-655.

TABLE 3

Selected geometric parameters (bond angles, degree) of Apn obtained from ab initio calculation and compared with reported crystal structure. Inset optimized geometry of Apn using restricted Hartree Fock level theory and 6-31G* basis set. Atom numbering of Apn is shown in FIG. 15.

| | crystal structure[a] | RHF/6-31G* |
|---|---|---|
| H1—O1—C1 | 111.0 | 110.65 |
| O1—C1—C2 | 122.13 | 122.94 |
| C1—C2—C3 | 119.9 | 119.94 |
| C2—C3—C4 | 120.89 | 120.19 |
| C3—C4—C5 | 118.98 | 118.61 |
| C4—C5—C6 | 120.09 | 120.08 |
| C5—C6—C1 | 120.72 | 120.96 |
| C6—C1—O1 | 118.47 | 117.85 |
| C6—C1—C2 | 119.40 | 119.19 |
| C4—N1—C7 | 128.41 | 129.18 |
| C4—N1—H2 | 116.0 | 114.76 |
| H2—N1—C7 | 115.4 | 116.05 |
| N1—C7—O2 | 123.2 | 124.36 |
| N1—C7—C8 | 115.11 | 113.64 |
| O2—C7—C8 | 121.72 | 121.99 |

[a]Naumov, D. Y.; Vasilchenko, M. A.; Howard, J. A. K. Acta Cryst. 1998, C54, 653-655.

Synthesis and Characterization of Acetaminophen Based Amphiphiles.

General procedure for synthesis of Apn-7-COOH and Apn-13-COOH. In a round bottom flask, α,ω-dicarboxylic acid (12 mmol) was dissolved in dry THF, to that 1.2 equivalent of DCC and catalytic amounts of DMAP was added at room temperature. After stirring for 1 hr, 4-Hydroxyacetanilide (1.36 g, 10 mmol) was added in one lot and stirring continued for 24 hrs. After completion of the reaction, mixture was filtered through cindered flask to remove DCU, washed with THF. After removal of THF, slightly acidic water was added, and thrice extracted with chloroform; organic layer was dried over anhydrous $Na_2SO_4$. After evaporating the solvent, the obtained crude products were purified by silica gel column chromatography using methanol:chloroform (1:9) as eluent, afforded pure products as white solid. Yields of the reactions were ~50%.

Apn-7-COOH. $^1$H-NMR, ($CDCl_3$, 300 MHz) δ 7.48 (d, 2H), 7.01 (d, 2H), 2.54 (broads, 1H), 2.35 (m, 4H), 2.15 (s, 3H), 1.70 (m, 4H), 1.5-1.2 (m, 4H).

Apn-13-COOH. $^1$H-NMR, ($CDCl_3$, 300 MHz) δ 7.50 (d, 2H), 7.05 (d, 2H), 2.57 (broads, 1H), 2.38 (m, 4H), 2.2 (s, 3H), 1.77 (m, 4H), 1.5-1.2 (m, 16H).

General procedure for synthesis of Apn-8-Apn and Apn-14-Apn. In a round bottom flask, α,ω-dicarboxylic acid (5 mmol) was dissolved in dry THF, to that 2.5 equivalent of DCC and catalytic amounts of DMAP was added at room temperature. After stirring for 1 hr, 4-Hydroxyacetanilide (1.36 g, 10 mmol) was added in one lot and stirring continued for 72 hrs. After completion of the reaction, mixture was filtered through cindered flask to remove DCU, washed with THF. After removal of THF, slightly acidic water was added, and thrice extracted with chloroform; organic layer was dried over anhydrous $Na_2SO_4$. After evaporating the solvent, the obtained crude products were purified by silica gel column chromatography using methanol:chloroform (0.5:9) as eluent, afforded pure products as white solid. Yields of the reactions were between 60-70%.

Apn-8-Apn. $^1$H-NMR, ($CDCl_3$, 300 MHz) δ 7.6 (d, 4H), 7.2 (d, 4H), 2.31 (broad s, 2H), 2.39 (m, 4H), 2.2 (s, 6H), 1.75 (m, 4H), 1.5-1.1 (m, 4H).

Apn-14-Apn. $^1$H-NMR, ($CDCl_3$, 300 MHz) δ 7.55 (d, 4H), 7.02 (d, 4H), 2.55 (broads, 2H), 2.41 (m, 4H), 2.18 (s, 6H), 1.75 (m, 4H), 1.6-1.1 (m, 16H).

Theoretical Calculation Methods.

The geometry of acetaminophen and its derivatives was fully optimized via ab initio calculations by using the restricted Hartree-Fock theory with 6-31G* basis set using GAUSSIAN 03 (Gaussian 03, Revision B.03, Frisch, M. J.; Trucks, G. W.; Schlegel, H. B.; Scuseria, G. E.; Robb, M. A.; Cheeseman, J. R.; Montgomery, Jr., J. A.; Vreven, T.; Kudin, K. N.; Burant, J. C.; Millam, J. M.; Iyengar, S. S.; Tomasi, J.; Barone, V.; Mennucci, B.; Cossi, M.; Scalmani, G.; Rega, N.; Petersson, G. A.; Nakatsuji, H.; Hada, M.; Ehara, M.; Toyota, K.; Fukuda, R.; Hasegawa, J.; Ishida, M.; Nakajima, T.; Honda, Y.; Kitao, O.; Nakai, H.; Klene, M.; Li, X.; Knox, J. E.; Hratchian, H. P.; Cross, J. B.; Adamo, C.; Jaramillo, J.; Gomperts, R.; Stratmann, R. E.; Yazyev, O.; Austin, A. J.; Cammi, R.; Pomelli, C.; Ochterski, J. W.; Ayala, P. Y.; Morokuma, K.; Voth, G. A.; Salvador, P.; Dannenberg, J. J.; Zakrzewski, V. G.; Dapprich, S.; Daniels, A. D.; Strain, M. C.; Farkas, O.; Malick, D. K.; Rabuck, A. D.; Raghavachari, K.; Foresman, J. B.; Ortiz, J. V.; Cui, Q.; Baboul, A. G.; Clifford, S.; Cioslowski, J.; Stefanov, B. B.; Liu, G.; Liashenko, A.; Piskorz, P.; Komaromi, I.; Martin, R. L.; Fox, D. J.; Keith, T.; Al-Laham, M. A.; Peng, C. Y.; Nanayakkara, A.; Challacombe, M.; Gill, P. M. W.; Johnson, B.; Chen, W.; Wong, M. W.; Gonzalez, C.; Pople, J. A. Gaussian, Inc., Pittsburgh Pa., 2003). Calculated Cartesian coordinates are shown in Tables 4-6.

TABLE 4

Calculated Cartesian coordinates for Apn

| | | | |
|---|---|---|---|
| 6 | 2.605874 | −0.218794 | −0.000932 |
| 8 | 2.520379 | −1.413547 | −0.000769 |
| 7 | 1.539481 | 0.628244 | −0.001902 |
| 1 | 1.753139 | 1.599461 | −0.001818 |
| 6 | 3.945796 | 0.490784 | 0.002427 |
| 1 | 4.042112 | 1.138871 | −0.862985 |
| 1 | 4.054076 | 1.100442 | 0.894075 |
| 1 | 4.729462 | −0.251314 | −0.018479 |
| 6 | 0.158994 | 0.325834 | −0.001042 |
| 6 | −0.729155 | 1.389986 | −0.000759 |
| 6 | −0.352592 | −0.970403 | −0.000591 |
| 6 | −2.098728 | 1.181397 | −0.000004 |
| 1 | −0.357860 | 2.400944 | −0.001129 |
| 6 | −1.718751 | −1.175710 | 0.000181 |
| 1 | 0.312612 | −1.806716 | −0.000836 |
| 6 | −2.600567 | −0.106508 | 0.000481 |
| 1 | −2.765416 | 2.027266 | 0.000195 |
| 1 | −2.114536 | −2.174314 | 0.000542 |

TABLE 4-continued

Calculated Cartesian coordinates for Apn

| | | | |
|---|---|---|---|
| 8 | −3.928022 | −0.380401 | 0.001207 |
| 1 | −4.434041 | 0.419708 | 0.001681 |

TABLE 5

Calculated Cartesian coordinates for Apn-7-COOH

| | | | |
|---|---|---|---|
| 6 | −7.766671 | 0.354033 | 0.000322 |
| 8 | −7.658978 | 1.546282 | 0.000817 |
| 7 | −6.713009 | −0.512227 | −0.001252 |
| 1 | −6.942284 | −1.480026 | −0.001270 |
| 6 | −9.117537 | −0.333146 | 0.004351 |
| 1 | −9.224976 | −0.978287 | −0.861896 |
| 1 | −9.234274 | −0.942362 | 0.895179 |
| 1 | −9.889043 | 0.421603 | −0.014532 |
| 6 | −5.331831 | −0.232714 | −0.001190 |
| 6 | −4.461451 | −1.313119 | −0.001768 |
| 6 | −4.800070 | 1.053887 | −0.000678 |
| 6 | −3.085683 | −1.147585 | −0.001801 |
| 1 | −4.854356 | −2.315708 | −0.002200 |
| 6 | −3.429357 | 1.222264 | −0.000705 |
| 1 | −5.445675 | 1.905055 | −0.000280 |
| 6 | −2.571513 | 0.136034 | −0.001241 |
| 1 | −2.445310 | −2.001611 | −0.002217 |
| 1 | −3.010634 | 2.211370 | −0.000322 |
| 8 | −1.233662 | 0.482398 | −0.001340 |
| 6 | −0.193431 | −0.350064 | −0.000546 |
| 8 | −0.266735 | −1.533968 | 0.000412 |
| 6 | 1.093206 | 0.440619 | −0.000856 |
| 6 | 2.340339 | −0.438076 | −0.000039 |
| 1 | 1.072511 | 1.096034 | 0.865353 |
| 1 | 1.072817 | 1.094872 | −0.867947 |
| 6 | 3.628351 | 0.386763 | −0.000357 |
| 1 | 2.319015 | −1.089047 | 0.868326 |
| 1 | 2.319334 | −1.090209 | −0.867542 |
| 6 | 4.888628 | −0.479899 | 0.000448 |
| 1 | 3.642525 | 1.039355 | −0.871461 |
| 1 | 3.642211 | 1.040515 | 0.869882 |
| 1 | 4.874503 | −1.132519 | 0.871581 |
| 1 | 4.874817 | −1.133678 | −0.869821 |
| 6 | 6.176617 | 0.344724 | 0.000132 |
| 6 | 7.424223 | −0.533270 | 0.000937 |
| 1 | 6.198357 | 0.996922 | 0.867519 |
| 1 | 6.198667 | 0.995771 | −0.868112 |
| 1 | 7.446415 | −1.187939 | 0.867940 |
| 1 | 7.446724 | −1.189085 | −0.865192 |
| 6 | 8.708587 | 0.254808 | 0.000646 |
| 8 | 8.803620 | 1.438826 | −0.000143 |
| 8 | 9.775844 | −0.542603 | 0.001347 |
| 1 | 10.554562 | 0.005512 | 0.001108 |

TABLE 6

Calculated Cartesian coordinates for Apn-8-Apn

| | | | |
|---|---|---|---|
| 6 | 12.028399 | 0.305826 | −0.008303 |
| 8 | 11.930570 | 1.498896 | −0.020573 |
| 7 | 10.967686 | −0.551783 | 0.002707 |
| 1 | 11.189210 | −1.521350 | 0.011993 |
| 6 | 13.373520 | −0.392437 | −0.005656 |
| 1 | 13.477879 | −1.024954 | 0.870242 |
| 1 | 13.482961 | −1.016303 | −0.887200 |
| 1 | 14.151294 | 0.356071 | −0.000175 |
| 6 | 9.588754 | −0.261421 | 0.000849 |
| 6 | 8.709964 | −1.334786 | 0.012493 |
| 6 | 9.066943 | 1.029337 | −0.011756 |
| 6 | 7.335402 | −1.158540 | 0.011870 |
| 1 | 9.094885 | −2.340422 | 0.022377 |
| 6 | 7.697685 | 1.208360 | −0.012425 |
| 1 | 9.719161 | 1.875377 | −0.020853 |
| 6 | 6.831254 | 0.128855 | −0.000776 |
| 1 | 6.688591 | −2.007651 | 0.020999 |
| 1 | 7.286632 | 2.200635 | −0.022106 |

TABLE 6-continued

Calculated Cartesian coordinates for Apn-8-Apn

| | | | |
|---|---|---|---|
| 8 | 5.496198 | 0.485778 | −0.003096 |
| 6 | 4.449457 | −0.338640 | 0.004787 |
| 8 | 4.513806 | −1.523015 | 0.015080 |
| 6 | 3.169013 | 0.461927 | −0.001539 |
| 6 | 1.915004 | −0.406909 | 0.006740 |
| 1 | 3.194192 | 1.108982 | −0.873900 |
| 1 | 3.195118 | 1.124153 | 0.859337 |
| 6 | 0.633556 | 0.428063 | 0.000175 |
| 1 | 1.930537 | −1.066143 | −0.855485 |
| 1 | 1.931505 | −1.051002 | 0.880316 |
| 6 | −0.633604 | −0.428466 | 0.008329 |
| 1 | 0.625260 | 1.088878 | 0.865162 |
| 1 | 0.624296 | 1.073720 | −0.876173 |
| 1 | −0.625325 | −1.089247 | −0.856682 |
| 1 | −0.624327 | −1.074156 | 0.884654 |
| 6 | −1.915052 | 0.406506 | 0.001823 |
| 6 | −3.169062 | −0.462328 | 0.010038 |
| 1 | −1.931566 | 1.050662 | −0.871702 |
| 1 | −1.930571 | 1.065680 | 0.864099 |
| 1 | −3.195179 | −1.124476 | −0.850889 |
| 1 | −3.194230 | −1.109465 | 0.882348 |
| 6 | −4.449506 | 0.338238 | 0.003820 |
| 8 | −4.513879 | 1.522610 | −0.006489 |
| 8 | −5.496255 | −0.486176 | 0.011252 |
| 6 | −6.831262 | −0.129096 | 0.008212 |
| 6 | −7.335253 | 1.158291 | 0.026149 |
| 6 | −7.697801 | −1.208391 | −0.011600 |
| 6 | −8.709778 | 1.334770 | 0.023164 |
| 1 | −6.688336 | 2.007243 | 0.041309 |
| 6 | −9.067029 | −1.029144 | −0.014482 |
| 1 | −7.286865 | −2.200674 | −0.024788 |
| 6 | −9.588684 | 0.261621 | 0.003015 |
| 1 | −9.094579 | 2.340404 | 0.036970 |
| 1 | −9.719343 | −1.875016 | −0.030021 |
| 7 | −10.967568 | 0.552203 | 0.001537 |
| 1 | −11.188979 | 1.521742 | 0.015385 |
| 6 | −12.028379 | −0.305197 | −0.014991 |
| 8 | −11.930692 | −1.498216 | −0.032336 |
| 6 | −13.373417 | 0.393196 | −0.007972 |
| 1 | −13.486330 | 0.998779 | 0.885788 |
| 1 | −13.474197 | 1.043658 | −0.871067 |
| 1 | −14.151234 | −0.354896 | −0.032138 |

REFERENCES CONSIDERED FOR EXAMPLE 1

1. *Hydrogels in Medicine and Pharmacy* (Ed: Peppas, N.) CRC, Boca Raton, Fla. 1987.
2. (a) Peppas, N. A.; Bures, P.; Leobandung, W.; Ichikawa, H. *Eur. J. Pharm. Biopharm.* 2000, 50, 27-46. (b) Peppas, N. *Curr. Opin. Colloid Interface Sci.* 1997, 2, 531-537.
3. (a) Gupta, P.; Vermani, K.; Garg, S. *Drug Discovery Today* 2002, 7, 569-579. (b) Miyata, T.; Uragami, T.; Nakamae, K. *Adv. Drug Deliv. Rev.* 2002, 54, 79-98. (c) Qiu, Y.; Park, K. *Adv. Drug Deliv. Rev.* 2001, 53, 321-339. (d) Kamath, K.; Park, K. *Adv. Drug Deliv. Rev.* 1993, 11, 59-84.
4. (a) Bryers, J. D.; Jarvis, R. A.; Lebo, J.; Prudencio, A.; Kyriakides, T. R.; Uhrich, K. *Biomaterials* 2006, 27, 5039-5048. (b) Erdmann, L.; Macedo, B.; Uhrich, K. E. *Biomaterials* 2000, 21, 2507-2512. (c) Harten, R. D.; Svach, D. J.; Schmeltzer, R.; Uhrich, K. E. *J. Biomed. Mater. Res-A* 2005, 72A, 354-362.
5. Huang, X.; Brazel, C. S. *J. Controlled Release* 2001, 73, 121-136.
6. Lee, K. Y.; Mooney, D. J. *Chem. Rev.* 2001, 101, 1869-1880.
7. van der Linden, H. J.; Herber, S.; Olthuis, W.; Bergveld, P. *Analyst* 2003, 128, 325-331.
8. Jen, A. C.; Wake, M. C.; Mikos, A. G. *Biotechnol. Bioeng.* 1996, 50, 357-364.
9. Wang, K.; Burban, J.; Cussler, E. *Hydrogels as separation agents. Responsive gels: volume transitions II* 1993 p. 67-79.
10. Bennett, S. L.; Melanson, D. A.; Torchiana, D. F.; Wiseman, D. M.; Sawhney, A. S. *J. Cardiac Surgery* 2003, 18, 494-499.
11. Peppas, N. A.; Hilt, J. Z.; Khademhosseini, A.; Langer, R. *Adv. Mater.* 2006, 18, 1345-1360, and references therein:
12. Hoare, T. R.; Kohane, D. S. *Polymer* 2008, 49, 1993-2007.
13. S. Lu, K. S. Anseth, *J. Controlled Release* 1999, 57, 291-300.
14. (a) Yang, Z.; Liang, G.; Xu, B. *Acc. Chem. Res.* 2008, 41, 315-326. (b) Yang, Z.; Liang, G.; Wang, L.; Xu, B. *J. Am. Chem. Soc.* 2006, 128, 3038-3043. (c) Yang, Z.; Gu, H. W.; Fu, D. G.; Gao, P.; Lam, K. J. K.; Xu, B. *Adv. Mater.* 2004, 16, 1440-1444. (d) Yang, Z.; Xu, B. *Chem. Commun.* 2004, 2424-2425.
15. (a) van Bommel, K. J. C.; Stuart, M. C. A.; Feringa, B. L.; van Esch, J. *Org. Biomol. Chem.* 2005, 3, 2917-2920. (b) Friggeri, A.; Feringa, B. L.; van Esch, J. *J. Controlled Release* 2004, 97, 241-248.
16. (a) Vemula, P. K.; Aslam, U.; Mallia, V. A.; John, G. *Chem. Mater.* 2007, 19, 138-140. (b) Vemula, P. K.; John, G. *Chem. Commun.* 2006, 2218-2220. (c) Jung, J. H.; John, G.; Masuda, M.; Yoshida, K.; Shinkai, S.; Shimizu, T. *Langmuir* 2001, 17, 7229-7232.
17. (a) Bhattacharya, S.; Maitra, U.; Mukhopadhyay, S.; Srivastava, A. *In Molecular Gels*; Terech, P., Weiss, R. G., Eds.; Kluwer Academic Publishers: The Netherlands, 2004. (b) Estroff, L. A.; Hamilton, A. D. *Angew. Chem. Int. Ed.* 2000, 39, 3447-3450.
18. Wang, G.; Hamilton, A. D. *Chem. Commun.* 2003, 310-311.
19. Kobayashi, H.; Friggeri, A.; Koumoto, K.; Amaike, M.; Shinkai, S.; Reinhoudt, D. N. *Org. Lett.* 2002, 4, 1423-1426.
20. Sreenivasachary, N.; Lehn, J.-M. *Proc. Natl. Acad Sci. USA* 2005, 102, 5938-5943.
21. Menger, F. M.; Caran, K. L. *J. Am. Chem. Soc.* 2000, 122, 11679-11691.
22. (a) Makarević, J.; Jokić, M.; Perčić, B.; Tomišić, V.; Krojić-Prodić, B.; inić, M. *Chem. Eur. J.* 2001, 7, 3328-3341. (b) Luboradzki, R.; Gronwald, O.; Ikeda, M.; Shinkai, S.; Reinhoudt, D. N. *Tetrahedron* 2000, 56, 9595-9599.
23. (a) Curran, S.; Murray, G. I. *Eur. J. Cancer* 2000, 36, 1621-1630. (b) Trouet, A.; Passiouskov, A.; van Derpoorten, K.; Fernandez, A. M.; Abarca-Quinones, J.; Baurian, R.; Lobl, T. J.; Oliyai, C.; Shochat, D.; Dubois, V. *Cancer Res.* 2001, 61, 2843-2846. (c) Rooseboom, M.; Commandeur, J. N. M.; Vermeulen, N. P. E. *Pharmacol. Rev.* 2004, 56, 53-102.
24. (a) Chourasia, M. K.; Jain, S. K. *J. Pharm. Pharmaceut. Sci.* 2003, 6, 22-66. (b) Sinha, V. R.; Kumaria, R. *Eur. J. Pharm. Sci.* 2003, 18, 3-18.
25. Vemula, P. K.; Li, J.; John, G. *J. Am. Chem. Soc.* 2006, 125, 8932-8938.
26. (a) Pina, L. A.; Sandrini, M.; Vitale, G. *Eur. J. Pharmacol.* 1996, 308, 31-40. (b) Boutaud, O.; Aronoff, D. M.; Richardson, J. H.; Marnett, L. J.; Oates, J. A. *Proc. Natl. Acad. Sci. USA* 2002, 99, 7130-7135.
27. Brodie, B. B.; Axelrod, J. *J. Pharmacol. Exp. Ther.* 1948, 94, 29-38.
28. (a) Hans, M.; Shimoni, K.; Danino, D.; Siegel, S. J.; Lowman, A. *Biomacromolecules* 2005, 6, 2708-2717. (b)

28. Kim, S. C.; Kim, D. W.; Shim, Y. H.; Bang, J. S.; Oh, H. S.; Wan-Kim, S.; Seo, M. H. *J. Controlled Release* 2001, 72, 191-202.
29. Frisch, M. J. et al. *Gaussian* 03, Revision B.03; Gaussian, In.: Pittsburg, Pa., 2003. For complete authors list see Supporting Information.
30. Hehre, W. J.; Radom, L.; Schleyer, P. V. R. *Ab Initio Molecular Orbital Theory*; Wiley & Sons: New York 1986. For description of basis sets and references, see pages 63-91.
31. Naumov, D. Y.; Vasilchenko, M. A.; Howard, J. A. K. *Acta Cryst.* 1998, C54, 653-655.
32. Jovanovic, S. V.; Boone, C. W.; Steenken, S.; Trinoga, M.; Kaskey, R. B. *J. Am. Chem. Soc.* 2001, 123, 3064-3068.
33. Duvoix, A.; Romain, B.; Sylvie, D.; Michael, S.; Franck, M.; Estelle, H.; Mario, D.; Marc, D. *Cancer Lett.* 2005, 223, 181-190.
34. Hergenhahn, M.; Ubaldo, S.; Annette, W.; Axel, P.; Chih-Hung, H.; Ann-Lii, C.; Frank, R. *Mol. Carcinog.* 2002, 33, 137-145.
35. Dahl, T. A.; Bilski, P.; Reszka, K. J.; Chignell, C. F. *Photochem. Photobiol.* 1994, 59, 290-294.
36. (a) Shim, J. S.; Kim, J. H.; Cho, H. Y.; Yum, Y. N.; Kim, S. H.; Park, H.-J.; Shim, B. S.; Choi, S. H.; Kwon, H. J. *Chem. Biol.* 2003, 10, 695-704. (b) Robinson, T. P.; Ehlers, T.; Hubbard IV, R. B.; Bai, X.; Arbiser, J. L.; Goldsmith, D. J.; Bowen, J. P. *Biorg. Med. Chem. Lett.* 2003, 13, 115-117.
37. Mazumder, A.; Raghavan, K.; Weinstein, J.; Kohn, K. W.; Pommier, Y. *Biochem. Pharm.* 1995, 49, 1165-1170.
38. Burke, T. R. Jr.; Fesen, M.; Mazumber, A.; Yung, J.; Wang, J.; Carothers, A. M.; Grunberger, D.; Driscoll, J.; Pommier, Y.; Kohn, K. *J. Med. Chem.* 1995, 38, 4171-4178.
39. Sui, Z.; Salto, R.; Li. J.; Craik, C.; Ortiz de Montellano, P. R. *Bioorg. Med. Chem.* 1993, 1, 415-422.
40. Khodpe, S. M.; Priyadarsini, K. I.; Palit, D. K.; Mukherjee, T. *Photochem. Photobiol.* 2000, 72, 625-631.
41. Tang, B.; Ma, L.; Wang, H.-Y.; Zhang, G.-Y. *J. Agric. Food Chem.* 2002, 50, 1355-1365.
42. Christenson, E. M.; Patel, S.; Anderson, J. M.; Hiltner, A. *Biomaterials* 2006, 27, 3920-3926.
43. Jahagirdar, B. N.; Verfaillie, C. M. *Stem Cell Rev.* 2005, 1, 53-59.

Example 2

Self-Assembling Amphiphiles

A series of amphiphiles were designed for efficient gelation. The amphiphile was synthesized in a single step that avoids the harsh conditions and is beneficial when synthesizing on an industrial scale. The use of expensive reagents was also eliminated. Compound purification was relatively easy. After the reaction, a simple filtration yielded a pure compound. Collectively these features make the amphiphile attractive for use in various biomedical applications.

This example focuses on a novel class of gelling agents or thickeners that are based on readily available and economically attractive starting materials. Gelling agents or thickeners capable of gelling or thickening a wide variety of solvents were used, making the gelling agents or thickeners suitable for employment in various applications.

Exemplary compounds include those having the general formula, $RCONHC(CH_2OH)_3$, in which R is a saturated alkyl chain having 9-15 C atoms or an unsaturated alkyl chain having 9-17 C atoms. N-tris(hydroxymethyl)methylamides of fatty acids, such as lauric, caprylic, myristic, palmitic, and oleic acids, can be prepared by reacting the fatty acids or their corresponding methyl esters with tris (hydroxymethyl)methylamine in anhydrous dimethylsulfoxide in the presence of potassium carbonate.

Results: These compounds have been found to produce a gel in numerous solvents. Examples of suitable solvents include water, salt water (such as a NaCl solution), different foreign bodies such as TRISZMA buffers, and alkaline and acidic solutions. In addition to water-based solutions, the compounds can gel various aromatic and non-aromatic organic solvents, such as benzene, toluene, hexane, and acetonitrile. See Table 7. All the gels obtained in Table 7 were thermally reversible. Above their gelation temperature, the gels dissolved in solvent, but could be returned to their original gel state upon cooling.

Figure 11B:
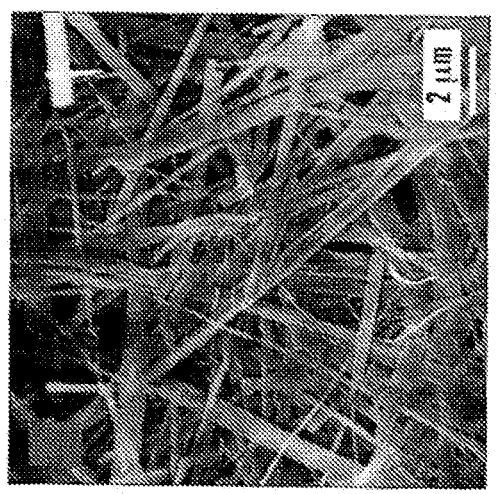
FIGS. 11A and 11B depict SEM images of (11A) organo and (11B) hydrogels formed by self-assembly of polyol-based amphiphiles.
Figure 11A:
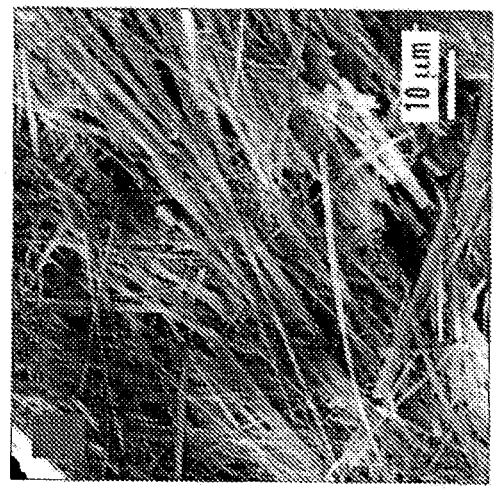

Scanning electron microscopic studies. Molecular self-aggregation features can be observed on an electron microscope, since the initial stage of physical gelation is the self-assembly of gelator monomers. FIGS. 11A and 11B show the scanning electron microscope (SEM) images of the organogels formed by the amphiphiles in cyclohexane and water, respectively. Analysis of these aggregates showed that the individual fibers are approximately 100-200 nm in wide and up to several micrometers in length. These nanofibers were entangled and formed a dense fibrous network, resulting in the immobilization of the solvent.

Figure 12:
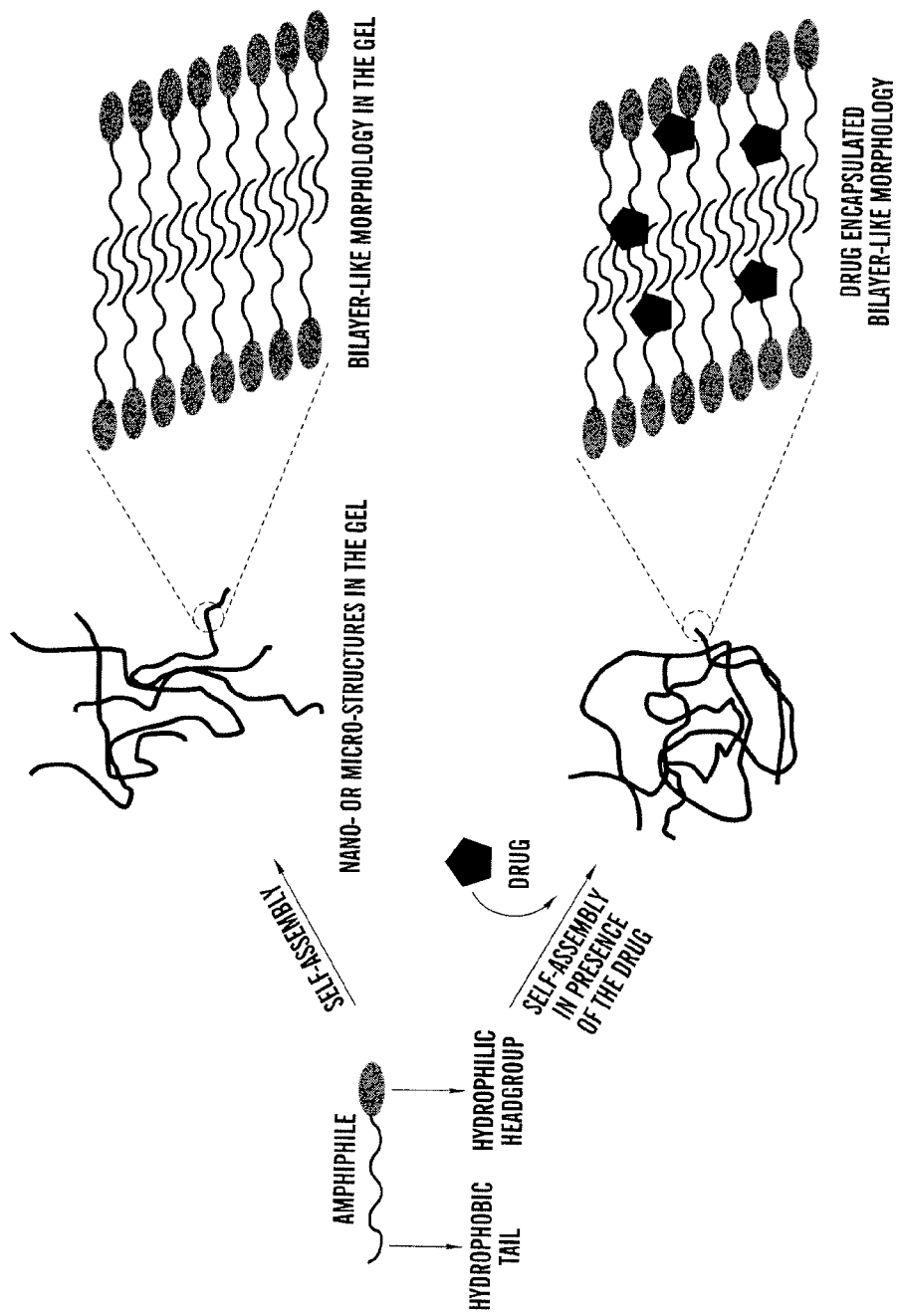
FIG. 12 is a schematic representation of self-assembly of amphiphiles to form gels and encapsulation of drugs in their assembled structures.
Figure 14A:
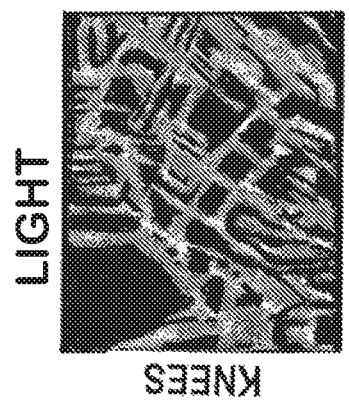
FIGS. 14A-14F depict optical microscope images of arthritis bearing mice joints at the knees (14A, 14B, and 14C represent light microscopic, fluorescence microscopic, and the merged image thereof, respectively) and at the ankles (14D, 14E and 14F represent light microscopic, fluorescence microscopic, and the merged image thereof, respectively), where the joints were injected with DiD encapsulated self-assembled nanofibers.
Figure 14B:
Figure 14C:
Figure 14D:
Figure 14E:
Figure 14F:
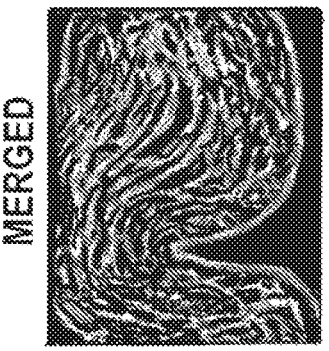

The examples demonstrate the encapsulation of hydrophobic and hydrophilic drugs in self-assembled hydrogels. Efficient encapsulation of various drugs enables the utilization of these gels for developing a wide range of therapeutics. A representative self-assembly of amphiphiles to fotin gels, and encapsulation of drugs in their nano- or micro structures is shown in FIG. 12.

TABLE 7

The gelation ability of polyol-12 and polyol-16 in water and various organic solvents.[a]

| solvent | polyol-12 | polyol-16 |
|---|---|---|
| water | G | G |
| NaCl (40 mM) | G | G |
| acidic (pH < 3) | G | G |
| basic (pH > 12) | G | G |
| TRIS (50 mM) | G | G |
| cyclohexane | G | G |
| benzene | G | G |
| toluene | G | G |
| $CCl_4$ | G | G |
| $CHCl_3$ | P | Sol |
| $CH_3CN$ | G | G |
| acetone | Sol | Sol |
| 1,4-dioxane | Sol | Sol |
| DMSO | Sol | Sol |

[a]G = stable gel at room temperature, P = precipitate, Sol = soluble.

REFERENCES CONSIDERED FOR EXAMPLE 2

1. Whitesides, G. M. & Boncheva, M. (2002) *Proc. Natl. Acad. Sci. USA* 99, 4769-4774.
2. Bong, D. T., Clark, T. D., Granja, J. R. & Ghadiri, M. R. (2001) *Angew. Chem. Int. Ed.* 40, 988-1011.
3. Lee, K. Y. & Mooney, D. J. (2001) *Chem. Rev.* 101, 1869-1879.
4. Friggeri, A., Feringa, B. L. & van Esch, J. (2004) *J. Controlled Release* 97, 241-248.

5. Yang, Z., Liang, G., Wang, L. & Xu, B. (2006) *J. Am. Chem. Soc.* 128, 3038-3043.
6. van Bommel, K. J. C., Stuart, M. C. A., Feringa, B. L. & van Esch, J. (2005) *Org. Biomol. Chem.* 3, 2917-2920.
7. Miyata, T., Uragami, T. & Nakamae, K. (2002) *Adv. Drug Delivery Rev.* 54, 79-98.
8. Menger, F. M. & Caran, K. L. (2000) *J. Am. Chem. Soc.* 122, 11679-11691.
9. Sreenivasachary, N. & Lehn, J.-M. (2005) *Proc. Natl. Acad. Sci. USA* 102, 5938-5943.
10. Makarević, J., Jokić, M., Perčić, B., Tomišić, V., Krojić-Prodić, B. & inić, M. (2001) *Chem. Eur. J.* 7, 3328-3341.
11. Oda, R., Hue, I. & Candau, S. J. (1998) *Angew. Chem. Int. Ed.* 37, 2689-2691.
12. Estroff, L. A. & Hamilton, A. D. (2000) *Angew. Chem. Int. Ed.* 39, 3447-3450.
13. Kobayashi, H., Friggeri, A., Koumoto, K., Amaike, M., Shinkai, S. & Reinhoudt, D. N. (2002) *Org. Lett.* 4, 1423-1426.
14. Luboradzki, R., Gronwald, O., Ikeda, M., Shinkai, S. & Reinhoudt, D. N. (2000) *Tetrahedron* 56, 9595-9599.
15. Jung, J. H., John, G., Masuda, M., Yoshida, K., Shinkai, S. & Shimizu, T. (2001) *Langmuir* 17, 7229-7232.
16. Wang, G. & Hamilton, A. D. (2003) *Chem. Commun.* 310-311.

Example 3

Dye Encapsulated Self-Assembled Nanofibers: In Vitro and in Vivo Analysis

In vitro. A model dye DiD was encapsulated within the self-assembled nanofibers prepared from salicin prodrug of formula (III). Salicin-deconate (4 wt/v %) was taken in glass vial and to that dye and PBS were added. Homogenous mixture was formed upon heating, subsequent cooling generated the gel. Fibers were isolated by repetitive centrifugation and washing steps. Fibers were incubated with synovial fluid at 37° C. that was extracted from human arthritic joints (inflamed). In the absence of synovial fluid, fibers were stable and preserved the dye within assembled fibers (FIG. 13A). The enzymes that were present in inflamed joints degraded the fibers to release the encapsulated dye. Slow degradation of fibers by enzymes over a period of 15 days was observed (FIG. 13B). The data demonstrates that in the absence of synovial fluid the fibers were intact and dye was confined to the fibers, whereas in the presence of synovial fluid, the fibers disassembled as observed by reduced number of fibers and by a drastic drop in the dye intensity. An accumulation of background fluorescence as the dye encapsulated fibers disassembled was also observed. In the absence of synovial fluid the nanofibers were stable (in PBS) for months.

In vivo: DiD encapsulated nanofiber gels (salicin-deconate nanofibers, prepared as above), were directly injected into the arthritis bearing mouse joints (ankles and knees) to examine the retention of nanofibers within the joints. After 8 days, ankles and knees were sectioned and imaged under fluorescence microscopy to examine the presence of nanofibers. Results shown in FIGS. 14A-14F indicate that dye encapsulated nanofibers were localized within the joints and a portion of the gel fibers originally injected can remain stable for long periods of time.

In vivo: DiD encapsulated nanofiber gels were directly injected into the arthritis bearing mouse joints (ankles and knees) to examine the retention of nanofibers within the joints. After 8 days, ankles and knees were sectioned and imaged under fluorescence microscopy to examine the presence of nanofibers. Results shown in FIGS. 14A-14F indicate that dye encapsulated nanofibers were localized within the joints and a portion of the gel fibers originally injected can remain stable for long periods of time.

The present invention may be defined in any of the following numbered paragraphs:

We claim:

1. A drug delivery gel composition comprising
   a hydrogel including precipitated highly organized self-assembled nanostructures comprising a plurality of self-assembling amphiphilic drug-derived gelators that associate by non-covalent interactions between the gelators,
   wherein the drug is selected from the group consisting of chemotherapeutic drugs, antibiotic drugs, analgesic, anti-pyretic, and anti-inflammatory drugs,
   the self-assembling amphiphilic drug-derived gelators forming the nanostructures comprising a drug headgroup conjugated via an ester to a tail group selected from the group consisting of fatty acids and dicarboxylic acids, prepared by esterifying the tail group to a group on the drug selected from the group consisting of phenol rings, terminal hydroxyl groups, saccharide groups, and primary hydroxyl groups,
   wherein the self-assembling amphiphilic drug-derived gelators associate by non-covalent interactions to self-assemble when exposed to a change in pH, temperature, in solvent type, concentration, or a combination thereof to form the hydrogel comprising nanoscale structures;
   wherein the hydrogel exhibits no gravitational flow upon inversion of the hydrogel at room temperature for ten minutes,
   and
   wherein the hydrogel and nanoscale structures controllably release the drug headgroup as the ester is hydrolyzed.

2. The gel composition of claim 1, wherein the headgroup is hydrophilic and the tail group is hydrophobic.

3. The gel composition of claim 1, wherein the headgroup is hydrophobic and the tail group is hydrophilic.

4. The gel composition of claim 1, wherein the drug is selected from the group consisting of analgesic drugs, anti-inflammatory drugs, and combinations thereof.

5. The gel composition of claim 4, wherein the drug comprises an anti-inflammatory drug selected from the group consisting of acetaminophen, salicin, indomethacin, and prodrugs and derivatives thereof.

6. The gel composition of claim 1, wherein the nanostructures are lamellar fiber structures which have a thickness of between about 50 and 400 nm.

7. The gel composition of claim 6, wherein the nanostructures are lamellar fiber structures which have a thickness of between about 100 and 200 nm.

8. The gel composition of claim 1, comprising one or more drugs encapsulated or entrapped by the nanostructures of the hydrogel.

9. The gel composition of claim 8, comprising two or more drugs.

10. The gel composition of claim 1, wherein the release of the drug is sustained release, not burst release.

11. The gel composition of claim 1, wherein the hydrogel is thermally reversible.

12. The gel composition of claim 1, wherein the rate of hydrolysis of the ester is proportional to the amount of infection.

13. The gel composition of claim 1, wherein the rate of hydrolysis of the ester is proportional to the amount of inflammation.

14. The gel composition of claim 1 prepared by self-assembly of a homogeneous aqueous solution.

15. The gel composition of claim 14 wherein the self-assembling amphiphilic drug-derived gelators are present at a concentration of greater than about 0.4 wt/vol % in the homogeneous aqueous solution.

16. The gel composition of claim 14 wherein self-assembly is driven by application of a stimulus that alters the solubility of the gelator.

17. The gel composition of claim 1 comprising drug at least partially encapsulated or entrapped by the nanoscale structures.

18. The gel composition of claim 1, wherein the fatty acid comprises a saturated or unsaturated $C_1$-$C_{21}$ alkyl chain.

19. The gel composition of claim 1, wherein the dicarboxylic acid is a $C_1$-$C_{22}$ dicarboxylic acid.

* * * * *